(12) United States Patent
Williams et al.

(10) Patent No.: US 9,522,005 B2
(45) Date of Patent: Dec. 20, 2016

(54) METHOD AND APPARATUS FOR FORMING STOMA TREPHINES AND ANASTOMOSES

(75) Inventors: Norman Stanley Williams, London (GB); Zhiqiang Weng, Sheung Wan (HK)

(73) Assignee: Queen Mary & Westfield College, London (GB)

( * ) Notice: Subject to any disclaimer, the term of this patent is extended or adjusted under 35 U.S.C. 154(b) by 860 days.

(21) Appl. No.: 13/228,729

(22) Filed: Sep. 9, 2011

(65) Prior Publication Data

US 2012/0061447 A1 Mar. 15, 2012

Related U.S. Application Data

(60) Provisional application No. 61/452,205, filed on Mar. 14, 2011.

(30) Foreign Application Priority Data

Sep. 9, 2010 (WO) ................ PCT/CN2010/076753

(51) Int. Cl.
*A61B 17/04* (2006.01)
*A61B 17/10* (2006.01)
(Continued)

(52) U.S. Cl.
CPC .......... *A61B 17/115* (2013.01); *A61B 17/1155* (2013.01); *A61B 17/02* (2013.01);
(Continued)

(58) Field of Classification Search
CPC ............ A61B 17/07207; A61B 17/068; A61B 2017/07278; A61B 2017/07271; A61B 17/1155; A61B 2017/07214; A61B 2090/0811; A61B 2017/00473; A61B 2017/00477; A61B 2017/2936; A61B 2017/2946; A61B 2017/2931
(Continued)

(56) References Cited

U.S. PATENT DOCUMENTS 3,895,636 A 7/1975 Schmidt
4,576,167 A 3/1986 Noiles
(Continued)

FOREIGN PATENT DOCUMENTS

CN 2282409 Y 5/1998
CN 1252255 A 5/2000
(Continued)

OTHER PUBLICATIONS

Keighley, M.R.B. & Williams, N.S., Surgery of the Anus Rectum and Colon, 3rd Ed., Saunders Ltd., 2008: Chapter 5, pp. 175-278.
(Continued)

*Primary Examiner* — Robert Long
(74) *Attorney, Agent, or Firm* — Pepper Hamilton LLP

(57) ABSTRACT

The present invention relates to a stapler apparatus, comprising a stapler having a proximal end, a distal end and a longitudinal axis, the stapler further comprising a trigger, an anvil docking pin aligned substantially parallel with the longitudinal axis of the stapler, and a stapling means, the anvil docking pin and stapling means being at the distal end of the stapler, and a detachable anvil, comprising an anvil head and an anvil shaft, wherein the anvil shaft is adapted to receive the anvil docking pin and operation of the trigger causes the stapling means to be actuated, characterised in that the length of the anvil shaft is at least 4 cm. The present invention also relates to a method of forming an anastomosis between two surfaces using the stapler apparatus of the invention and a method of forming a stoma trephine in a subject using the stapler apparatus of the invention. The
(Continued)

present invention further relates to the use of the stapler apparatus or anvil for a stapler apparatus in such methods and a kit of parts comprising the stapler apparatus of the invention and additional components.

21 Claims, 21 Drawing Sheets

(51) Int. Cl.
*A61B 17/115* (2006.01)
*A61B 17/02* (2006.01)
*A61B 17/072* (2006.01)
*A61B 17/00* (2006.01)
*A61B 17/11* (2006.01)

(52) U.S. Cl.
CPC . *A61B 17/07292* (2013.01); *A61B 2017/0023* (2013.01); *A61B 2017/00818* (2013.01); *A61B 2017/0287* (2013.01); *A61B 2017/1142* (2013.01); *A61B 2090/0808* (2016.02); *A61B 2090/0811* (2016.02)

(58) Field of Classification Search
USPC .......................................... 227/175.1–182.1
See application file for complete search history.

(56) References Cited

U.S. PATENT DOCUMENTS

| | | | |
|---|---|---|---|
| 4,930,674 A * | 6/1990 | Barak | 227/179.1 |
| 5,205,459 A * | 4/1993 | Brinkerhoff | A61B 17/115 227/179.1 |
| 5,318,040 A | 6/1994 | Kensey et al. | |
| 5,325,866 A | 7/1994 | Krzyzanowski | |
| 5,441,191 A * | 8/1995 | Linden | 227/120 |
| 5,535,754 A | 7/1996 | Doherty | |
| 5,669,918 A | 9/1997 | Balazs et al. | |
| 5,674,203 A * | 10/1997 | Lewandowski | 604/197 |
| 5,685,474 A * | 11/1997 | Seeber | 227/179.1 |
| 5,758,814 A | 6/1998 | Gallagher et al. | |
| 6,050,472 A * | 4/2000 | Shibata | A61B 17/115 227/175.2 |
| 6,053,933 A | 4/2000 | Balazs et al. | |
| 7,318,830 B2 | 1/2008 | Mayoral | |
| 7,401,722 B2 | 7/2008 | Hur | |
| 7,422,138 B2 | 9/2008 | Bilotti et al. | |
| 7,431,191 B2 * | 10/2008 | Milliman | 227/179.1 |
| 7,547,312 B2 | 6/2009 | Bauman et al. | |
| 7,942,302 B2 * | 5/2011 | Roby et al. | 227/175.1 |
| 8,181,838 B2 * | 5/2012 | Milliman et al. | 227/175.1 |
| 8,231,042 B2 * | 7/2012 | Hessler et al. | 227/179.1 |
| 8,348,122 B2 * | 1/2013 | Milliman et al. | 227/175.1 |
| 8,393,516 B2 * | 3/2013 | Kostrzewski | 227/180.1 |
| 8,485,414 B2 * | 7/2013 | Criscuolo et al. | 227/179.1 |
| 8,496,157 B2 * | 7/2013 | Olson | 227/179.1 |
| 8,684,251 B2 * | 4/2014 | Rebuffat et al. | 227/179.1 |
| 8,684,254 B2 * | 4/2014 | Kostrzewski | 227/180.1 |
| 8,733,611 B2 * | 5/2014 | Milliman | 227/175.2 |
| 2003/0236529 A1 | 12/2003 | Shluzas et al. | |
| 2004/0217146 A1 * | 11/2004 | Beck | 227/176.1 |
| 2005/0023325 A1 | 2/2005 | Gresham et al. | |
| 2006/0155326 A1 | 7/2006 | Aranyi | |
| 2009/0230170 A1 * | 9/2009 | Milliman | A61B 17/0686 227/176.1 |
| 2010/0089971 A1 | 4/2010 | Milliman et al. | |
| 2010/0096435 A1 | 4/2010 | Fuchs et al. | |
| 2010/0282816 A1 * | 11/2010 | Scirica et al. | 227/176.1 |
| 2010/0327041 A1 * | 12/2010 | Milliman et al. | 227/175.1 |
| 2011/0011915 A1 * | 1/2011 | Shelton, IV | 227/176.1 |
| 2011/0036891 A1 * | 2/2011 | Zemlok et al. | 227/176.1 |
| 2011/0095067 A1 | 4/2011 | Ohdaira | |
| 2011/0095070 A1 * | 4/2011 | Patel et al. | 227/181.1 |
| 2012/0065665 A1 * | 3/2012 | Williams | A61B 17/115 606/207 |
| 2014/0367444 A1 * | 12/2014 | Williams | 227/175.1 |

FOREIGN PATENT DOCUMENTS

| | | |
|---|---|---|
| CN | 2448296 Y | 9/2001 |
| CN | 2492196 Y | 5/2002 |
| CN | 101011277 A | 8/2007 |
| CN | 201205297 Y | 3/2009 |
| CN | 101569547 Y | 11/2009 |
| EP | 0074878 A2 | 3/1983 |
| EP | 0536882 A2 | 4/1993 |
| EP | 0570915 | 5/1993 |
| EP | 0908150 A2 | 4/1999 |
| EP | 2153781 A2 | 2/2010 |
| EP | 2184018 A2 | 5/2010 |
| JP | 1992133811 | 12/1992 |
| JP | 1998151138 | 6/1998 |
| JP | 2000201939 | 7/2000 |
| JP | 2007516730 | 6/2007 |
| JP | 2007252910 | 10/2007 |
| JP | 2007289673 | 11/2007 |
| JP | 2007319511 | 12/2007 |
| JP | 2008518714 | 6/2008 |
| JP | 2009291492 A2 | 12/2009 |
| WO | 01/66020 A2 | 9/2001 |
| WO | 2004/089255 A1 | 10/2004 |
| WO | 2006/075153 A1 | 7/2006 |
| WO | 2007/121238 A2 | 10/2007 |
| WO | 2008/101497 A1 | 8/2008 |
| WO | 2009/137761 A2 | 11/2009 |
| WO | 2009133875 | 11/2009 |

OTHER PUBLICATIONS

Williams, N. S., et al., EXternal Pelvic REctal SuSpension (Express procedure) for rectal intussusception, with and without rectocele repair, Br. J. Surg., May 2005;92(5):598-604.

Williams, N. S., et al., Anterior Perineal PlanE for Ultra-low Anterior Resection of the Rectum (the APPEAR technique): a prospective clinical trial of a new procedure, Ann Surg., May 2008;247(5):750-758.

Single Use Curved Intraluminal Circular Stapler, Product Brochure, Frankenman International Limited (obtained from website http://www.frankenman.com prior to the priority date of the current application).

El-Gendy, K. A., et al., Anterior Perineal PlanE for Ultralow Anterior Resection of the Rectum (the APPEAR Technique): a video demonstration, Ann Surg Oncol. May 2010;17(5):1357-8. Epub Dec. 29, 2009.

Fazio, V., W., Rob and Smith's Operative Surgery: Alimentary tract and abdominal wall: Colon, Rectum and Anus, 4th edition, 1983, pp. 54-62 & 91-93, published by Butterworths and edited by Ian P. Todd and L. P. Fielding.

Non-Final Official Action dated Dec. 3, 2013 received in related U.S. Appl. No. 13/228,542.

Notice of Allowance dated Jun. 23, 2014 issued in related U.S. Appl. No. 13/228,542.

* cited by examiner

METHOD AND APPARATUS FOR FORMING STOMA TREPHINES AND ANASTOMOSES

CROSS-REFERENCE TO RELATED APPLICATIONS

This application claims priority to U.S. provisional application Ser. No. 61/452,205 filed Mar. 14, 2011 and International Application No. PCT/CN2010/076753 filed Sep. 9, 2010, each of which is incorporated herein by reference in its entirety.

FIELD OF THE INVENTION

The current invention relates to a method and apparatus for the creation of stoma trephines and anastomoses in hollow organs in both open and laparoscopic approaches.

BACKGROUND OF THE INVENTION

A number of diseases require segmental resection to remove part of an organ. For example, inflammatory diseases of the bowel (e.g. Crohn's disease, ulcerative colitis), colorectal cancer and bowel infarction may require removal of a section of the lower gastrointestinal (GI) tract. Following resection, the two ends of the GI tract must be reattached to one another to allow continued functioning. The process of this reattachment is known as surgical anastomosis.

A stoma is an artificial opening between two hollow organs or between one hollow organ and the outside of the body. The creation of artificial stomas such as colostomies, ileostomies, urostomies, oesophagostomies, and gastrostomies can be a useful medical intervention in disease treatment where the normal visceral tract must be bypassed to allow, for example, the discharge of waste or delivery of nutrition from/to the body.

Historically, anastomoses and stomas were achieved using conventional sutures. The conventional technique for stoma trephine construction involves stretching of the defect through the abdominal wall usually to accommodate the breadths of the surgeon's index and second fingers at the position of the second interphalangeal joints (Keighley, M. R. B. & Williams, N. S., "Surgery of the Anus Rectum and Colon", 3rd Ed., Saunders Ltd., 2008). Such relatively uncontrolled stretching of the abdominal wall and particularly the rectus abdominis muscle is likely to result in weakness of the abdominal wall at the site of trephine creation with subsequent widening of the defect over time resulting in hernia formation. Surgical staplers have occasionally been described for stoma construction. Surgical staplers are more frequently used for anastomoses.

Conventionally, surgical circular staplers are used for anastomosis of hollow tubular organs, for example bowel, oesophagus and other tubular structures. Circular staplers can deliver two or more circumferentially mounted rows of staples to secure opposing sides of the tubular organ together. Simultaneously an internal circular cutting blade mounted in a stapler housing creates an internal lumen allowing normal functioning of lumen to be reconstituted following excision of diseased portions of the tubular organ. "Circular" refers to the substantially circular arrangement of staples that is delivered by the stapler.

Circular staplers in current use generally comprise an anvil and a stapler. The anvil docks onto the stapler via an anvil docking pin present on the stapler. However, the construction of current stapling devices restricts docking of the elements, namely the stapler anvil to the stapler, to within the body lumen. Certain new procedures or elements of current procedures would benefit, in terms of efficacy and safety, if this docking could be externalised.

Example circular staplers are described in WO 2004/089225, U.S. Pat. Nos. 4,576,167, 7,422,138, 7,318,830 and 7,547,312, the contents of which are incorporated herein by reference.

Contemporary colorectal surgery attempts to strike a balance between effecting disease cure and preservation of anatomy and function. Regrettably, this remains strikingly evident in the treatment of low rectal cancer when complete excision of the anorectum (APER) and the formation of permanent end colostomy are often still necessary to optimise oncological cure. Sphincter preservation in such patients is secondary to oncological cure and anorectum and normal anorectum functions sacrificed resulting in permanent colostomy with all the life affecting results, which have been well documented in the medical and public domains. Resolving this compromise has perhaps become the 'holy grail' of modern coloproctology.

Several techniques have been described to help secure an ultra-low anastomosis e.g. abdomino-trans-sacral, abdomino-transanal, abdomino-trans-sphincteric or inter-sphincteric. Each of these is technically extremely difficult to perform and may damage sphincteric mechanisms significantly with consequent severely impaired continence. As a result, these have not been widely adopted.

In addition to loss of sphincter function following low and ultra-low ileo or colo-rectal anastomosis, parastomal herniation is an extremely common complication following stoma formation, with a reported incidence of up to 48% over a 10-year period. Risk factors include obesity, malignancy, poor nutrition, steroid therapy and conditions which raise intra-abdominal pressure (Keighley and Williams, 2008). Loop stomas seem to be particularly prone to this complication, presumably because its construction requires a larger abdominal trephine compared with an end stoma. Such hernias cause considerable morbidity such as local pain and intestinal obstruction which may necessitate emergency surgery and bowel resection with a risk of mortality.

In the course of surgery to correct proctographic abnormalities in patients with disordered rectal evacuation, the inventors have used an anterior perineal approach to expose the plane between the rectum and vagina (or prostate) (Williams, N. S. et al., Br J Surg; 2005; 92:598-604). It became evident from such procedures that relatively easy access to the lower rectum and anal canal could be gained whilst allowing the external and internal anal sphincters to be retained intact. Indeed, the inventors have now demonstrated during open surgery the utility and safety of this approach, which is termed the APPEAR (Anterior Perineal PlanE for Anterior Resection) technique (Williams, N. S. et al., Ann Surg; 2008; 247:750-758), as an adjunct to performing conventional rectal excisional surgery in the context of low rectal carcinoma and large villous adenoma.

The resection and subsequent anastomosis of diseased pathology in the lower rectum, specifically the last 10 cms and in particular the last 5 cm of the rectum, is problematic using conventional stapling techniques where the position of the resection on the anal side is extremely low relative to the anal verge or there is insufficient space in the perineal cavity, created during the APPEAR procedure, to adequately bring the opposing anvil shaft and trocar (anvil docking pin) elements into approximation for docking.

There remains in the art a need for a surgical device and technique that allows construction of low and ultra-low ileo of colo-rectal anastomoses whilst maintaining sphincter integrity and thus continence. There also remains in the art a need for a surgical device and technique that allows the formation of stomas which avoid the problems such as parastomal hernias.

SUMMARY OF THE INVENTION

The inventors have identified and developed a specific procedure where the addition of endo-anal or extracorporeal docking capabilities would provide distinct procedural advantages and have developed a method of surgical practice as well as a suite of iterations and accessories to conventional devices to facilitate these procedural improvements. Other procedures may also benefit from surgical staplers with endo-anal or extracorporeal docking capabilities.

Consequently the inventors have developed a modified procedure and novel facilitating devices specifically to compensate for the anatomical and procedural difficulties, namely an endo-anal or extracorporeal surgical stapler apparatus.

The new stapler apparatus is suitable for creating both anastomoses and stoma trephines whilst reducing the side effects such as loss of sphincter control and parastomal hernias.

Accordingly, in a first aspect of the invention there is provided a stapler apparatus, comprising:

(a) a stapler having a proximal end, a distal end and a longitudinal axis, the stapler further comprising:
  (i) a trigger;
  (ii) an anvil docking pin aligned substantially parallel with the longitudinal axis of the stapler; and
  (iii) a stapling means, the anvil docking pin and stapling means being at the distal end of the stapler; and
(b) a detachable anvil comprising an anvil head and an anvil shaft, wherein the anvil shaft is adapted to receive the anvil docking pin and operation of the trigger causes the stapling means to be actuated, characterised in that the length of the anvil shaft is at least 4 cm.

As a result of the specific length of the anvil shaft, the anvil is easier to manipulate and allows endo-anal or extracorporeal engagement of the anvil with the stapler.

The invention also relates to an anvil for a surgical stapler comprising an anvil head and an anvil shaft, characterised in that the length of the anvil shaft is at least 4 cm.

The invention also relates to the use of the stapler apparatus of the invention or anvil for a surgical stapler in the formation of an anastomosis.

The invention further relates to the use of the stapler apparatus of the invention or anvil for a surgical stapler in the formation of a stoma trephine.

The invention also relates to a method of forming an anastomosis between two surfaces using the stapler apparatus of the invention comprising attaching a first surface to be stapled to the anvil of the stapler apparatus, engaging the anvil docking pin with the anvil shaft, positioning the stapler to engage the stapling means with the second surface to be stapled, and activating the stapling means to connect together the first and second surfaces with staples.

The invention also relates to a method of forming a stoma trephine in a subject comprising forming an incision in the subject where a stoma is to be formed, positioning an anvil of the stapler apparatus of the invention such that the anvil head is inside the subject and the anvil shaft is projecting through the incision, docking the anvil shaft onto the anvil docking pin of the stapler, and activating the stapling means to dispense a series of staples in the tissue being stapled.

The invention also relates to a kit of parts comprising the stapler apparatus of the invention and a safety guard.

DETAILED DESCRIPTION

Endo-anal (or extracorporeal) docking is an adjunct technique developed by the inventors to facilitate APPEAR in cases of ultra low resection and anastomosis from within approximately 2 to 10 cm from the anal verge depending on the patient's body habitus. Until the development of the APPEAR technique, access to this part of the distal ano-rectum (whilst also preserving the complete integrity of the anal sphincter mechanism and its somatic nerve supply) was not possible. By providing relatively easy access to the lower rectum and anal canal, and preserving the internal and external sphincters, in most cases the need for permanent stoma creation can be prevented.

Accordingly, the present invention relates to a stapler apparatus adapted for extracorporeal or endo-anal docking of the anvil shaft to the stapler as required in procedures such as APPEAR (a recently developed approach to sphincter-preserving/ultra low colo-or ileo-anal anastomosis) and other potential procedures that require extracorporeal docking of anvil and stapler components with clear and precise indication that the elements are firmly and safely attached to one another, for example the formation of stoma trephines.

Figure 1:
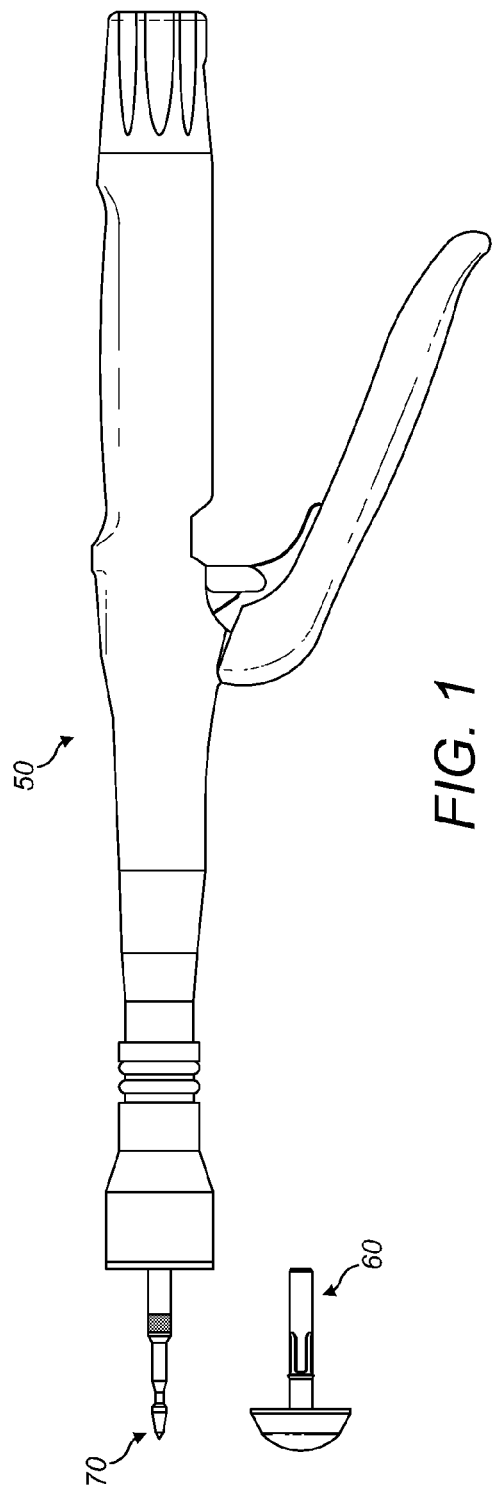
FIG. 1 shows a stapler apparatus comprising a stapler 50 with a conventional anvil docking pin 70 and a conventional anvil 60.
Figure 2:
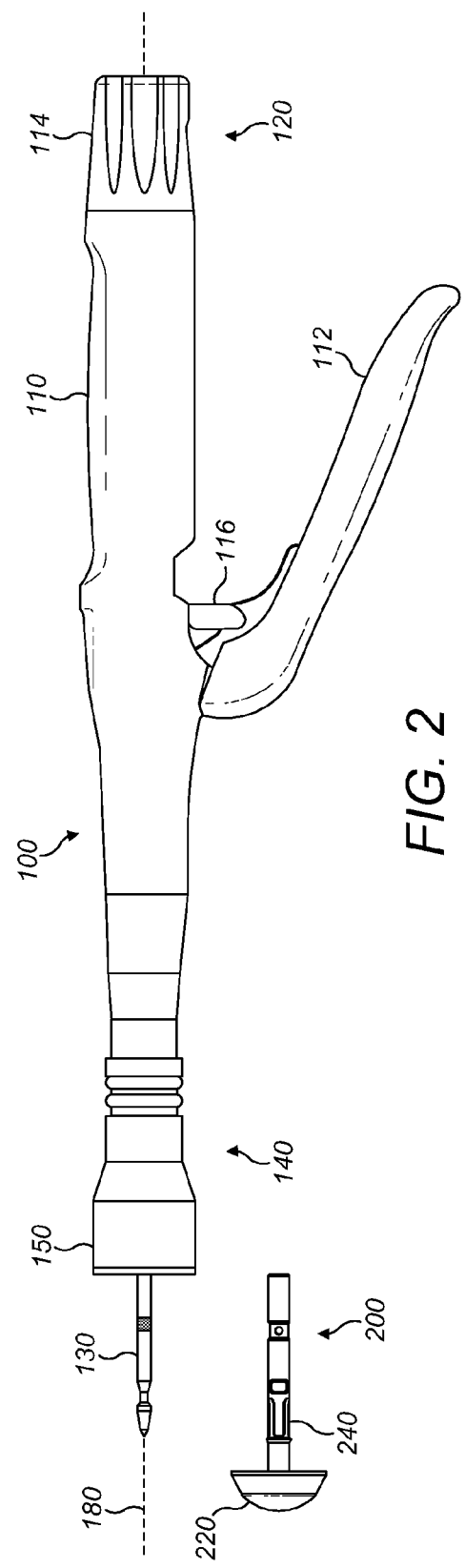
FIG. 2 shows stapler apparatus of the invention comprising a stapler 100 and an anvil 200.
Figure 3:
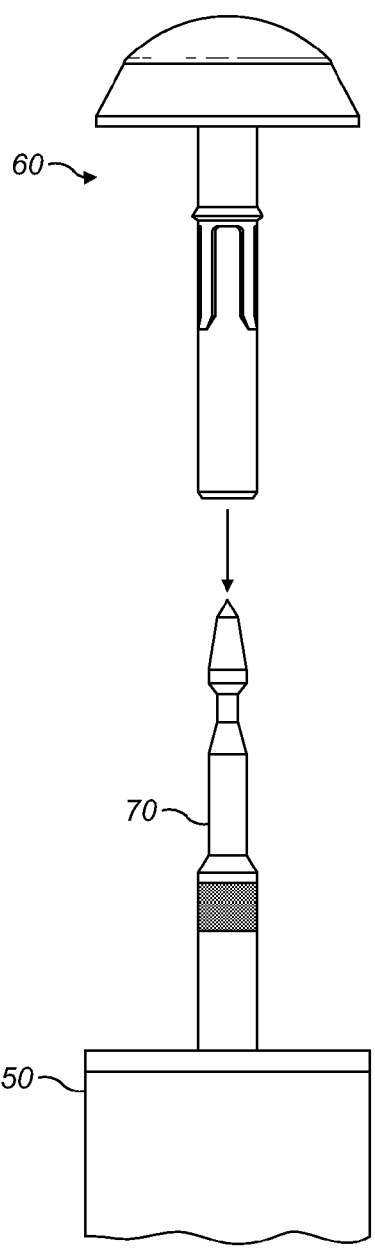
FIG. 3 shows the docking of a conventional anvil 60 onto the conventional anvil docking pin 70 of a stapler 50.

The stapler apparatus of the invention as shown in FIG. 2 comprises:

(a) a stapler 100 having a proximal end 120, a distal end 140 and a longitudinal axis 180, the stapler 100 further comprising
  (i) a trigger 112;
  (ii) an anvil docking pin 130 aligned parallel with the longitudinal axis 180 of the stapler 100; and
  (iii) a stapling means 150, the anvil docking pin 130 and stapling means 150 being at the distal end 140 of the stapler 100; and
(b) a detachable anvil 200, comprising an anvil head 220 and an anvil shaft 240, wherein the anvil shaft 240 is adapted to receive the anvil docking pin 130 and operation of the trigger 112 causes the stapling means 150 to be actuated, characterised in that the length of the anvil shaft 130 is at least 4 cm.

References to the "proximal" and "distal" ends of the stapler refer to the relative distance of the two ends of the stapler from the user when the stapler apparatus is being operated. The proximal end is that closest to the user and so usually comprises a grip area and trigger for actuation of the stapling means. The distal end is further away from the user, but is closer to the patient to whom the stapling apparatus is being applied, and so in general is where the stapling means and anvil docking pin are situated.

Generally, the longitudinal axis extends between the proximal and distal ends and passes substantially through the centre of the stapler.

Figure 9:
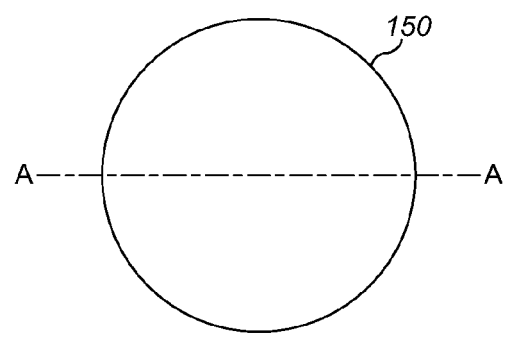
FIG. 9 shows the cross section of the stapling means through the line A-A of FIG. 7.

References to "circular" include substantially circular and other configurations which would be apparent to a person of skill in the art that provides an appropriate arrangement of staples. For example, as shown in FIG. 9, the cross section of the stapling means can be circular so as to be able to provide a substantially circular configuration of staples, although an elliptical arrangement can also be used. Generally, the anvil head, the anvil shaft, the anvil docking pin and the stapling means are all substantially circular in cross section, although other arrangements may be possible provided they are able to deliver a suitable arrangement of staples.

The stapler generally has an elongate body, preferably a substantially cylindrical body. It is preferably shaped so as to allow insertion into the appropriate tissues and organs The body of the stapler includes a trigger 112 and a stapling means 150. Preferably, the body of the stapler is substantially straight and is not bent or curved. This is useful depending on the anatomy and organs to which the stapler apparatus is being applied. In those embodiments where the body of the stapler is straight or substantially straight (as opposed to bent or curved), this also provides greater control over the stapler since there are less oscillations and movement during operation, which has an impact on the quality of the anastomosis or stoma trephine. For example, the stapler can be kept parallel to the rectal wall more easily than if the stapler was curved.

In some embodiments, the stapler comprises a grip area 110 which is intended to be held by the user when the stapler is being employed. The grip area is usually positioned towards the proximal end 120 of the stapler (stapling can therefore be carried out at a distance from the user), although may be present elsewhere on the stapler.

The stapler apparatus of the invention can be used in a variety of open, endoscopic or laparoscopic surgical applications, for example the formation of anastomoses, stomas or stoma trephines. These can be in, for example, the gastrointestinal (GI) tract or between the GI tract and the exterior of the body, but more generally could be used in any tubular organs or those organs having a lumen. The stapler apparatus is therefore suitable as a surgical stapler or, in some more specific embodiments, as an intraluminal stapler. Moreover, given the substantially circular arrangements of staples delivered in some embodiments of the invention, the apparatus can be said to be a circular stapler apparatus.

Usually the stapler apparatus is disposable and will be disposed of after use. In preferred embodiments, the stapler apparatus is sterile.

In some embodiments, the length of the anvil shaft is 4, 5, 6, 7, 8, 9 to 10 cm in length. In some embodiments, the length of the anvil shaft is at least 4, 5, 6, 7, 8, 9 to 10 cm in length. In some preferred embodiments, the length of the anvil shaft is in the range of 4 to 50 cm, more preferably in the ranges of 4 to 25 cm, 4 to 20 cm, 4 to 15 cm, 4 to 12 cm, 4 to 10 cm, 5 to 50 cm, 5 to 25 cm, 5 to 20 cm, 5 to 15 cm, 5 to 12 cm, 5 to 10 cm, 6 to 50 cm, 6 to 25 cm, 6 to 20 cm, 6 to 15 cm, 6 to 12 cm or 6 to 10 cm.

In some embodiments of the invention, the overall working length of the stapler has been reduced from the industry standard of 420 mm to between 250 to 400 mm, preferably between 300 and 350 mm, more preferably between 310 and 340 mm, and most preferably between 320 and 330 mm or to 325 mm. This reduced overall working length of the stapler provides a better, more stable and ergonomic platform to enhance user control of the stapler device during manipulation and firing of stapler apparatus.

The anvil of the stapler apparatus of the current invention is elongated compared to the anvils of the prior art, and this elongation of the anvil shaft provides several advantages over the prior art.

For example, since there is a longer anvil shaft, the anvil is more easily manipulated by the user and moreover it is possible to carry out the docking procedure endo-anally or extracorporeally.

The elongated shaft also allows the anvil to be grasped by the surgeon endoanally or extracorpoeally, or allows the surgeon to grasp it internally and bring the anvil shaft into an endo-anal or extracorporeal position. This allows the surgeon to see more clearly where the anvil is to aid docking onto the anvil docking pin. The elongated shaft also allows the surgeon to see extracorporeally that the anvil has fully engaged with the stapler. Hence the elongated shaft provides a visualisation advantage over the prior art. In staplers of the prior art, the anvil shaft is obscured or surrounded by tissue that makes it difficult to locate the anvil shaft or difficult to grasp the shaft in order to manoeuvre it into position. However, extending the anvil shaft of the current invention removes this problem.

Moreover, since the anvil shaft is more easily seen by the surgeon, it is also easier for the surgeon to ensure that complete docking of the anvil shaft on the anvil docking pin is achieved. Staplers of the prior art rely on an audible "click" alone to ensure docking In contrast, the stapler of the present invention additionally provides visual confirmation that docking has occurred. Hence the stapler of the present invention provides additional safety for the patients.

The elongated anvil shaft enables passage from internal body habitus to the endo-anal or extracorporeal space for docking to the stapler. The length of this elongation is only limited by modifications to interior drive shafts of the stapler that facilitate movement (retraction and extension) of the anvil docking pin and engaged anvil shaft into and out of the stapler.

Before the realisation of the current invention with the extended anvil shaft, it was impossible to perform endo-anal or extracorporeal docking of the anvil to the anvil docking pin due to the limitations inherent in the staplers of the prior art.

Since the stapler apparatus of the invention allows creation of an anastomosis with endo-anal or extracorporeal docking even in cases of ultra low resection and anastomosis from within approximately 2 to 10 cm from the anal verge (as in the APPEAR technique), it allows a larger section of bowel to be removed without necessarily leading to sphincter removal. For example, in cases of ulcerative colitis or colorectal cancer, larger sections of bowel can be removed to avoid retention of diseased rectum whilst maintaining faecal continence.

Figure 4:
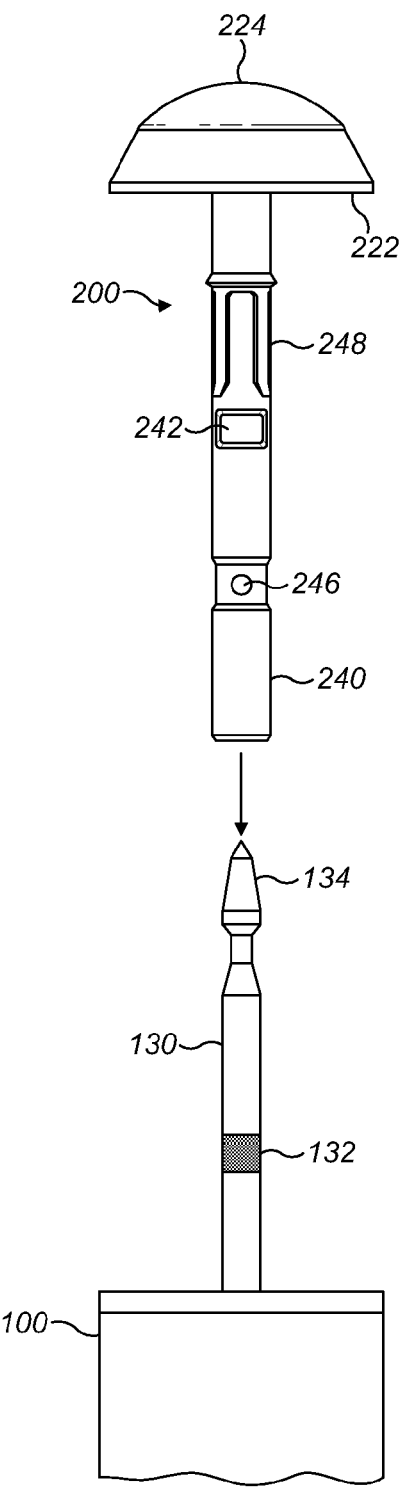
FIG. 4 shows an anvil of the invention 200 aligned ready for docking onto the anvil docking pin 130 of a stapler of the invention 100.
Figure 5:
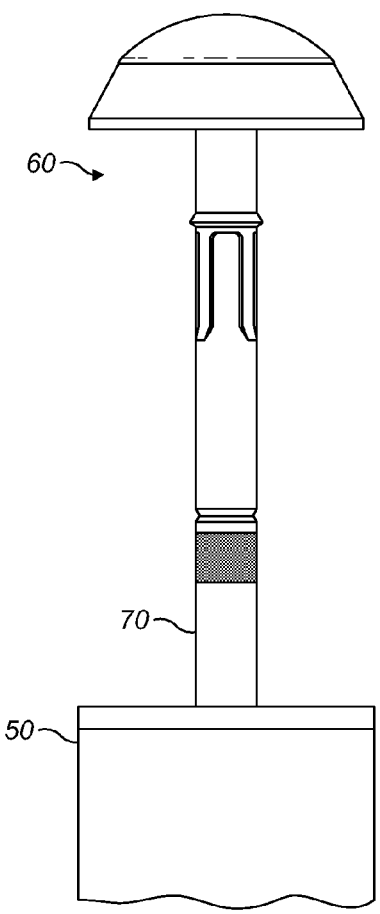
FIG. 5 shows a stapler apparatus wherein the conventional anvil 60 is fully engaged with the conventional anvil docking pin 70.

The anvil docking pin according to the invention can be similarly altered in length to accommodate the different lengths of the anvil shaft. Usually, the anvil docking pin extends into the stapler such that only a section of the anvil docking pin is visible when the stapler is viewed from the side, as in FIG. 2. The anvil docking pin has a smaller diameter than the anvil shaft, allowing the anvil docking pin to be inserted into the anvil shaft. In particular, the anvil docking pin has a diameter equal to or less than the internal chamber 241 of the anvil shaft 240, as shown in FIG. 4. In a preferred embodiment, the anvil docking pin is aligned coaxially or substantially coaxially (for example, within a distance that is equal to or less than the width or diameter of the anvil docking pin, or any distance that allows a suitably spaced distribution of staples around the anvil docking pin) with the longitudinal axis of the stapler.

The anvil docking pin according to the invention can be blunt or it can be trocar tipped. A trocar tipped anvil docking pin, such as that shown in FIG. 4, has the advantage of being able to pierce tissues. For example, when creating an anastomosis in the lower rectum, the rectal stump may be closed off using sutures or staples and the trocar tipped anvil docking pin can be used to pierce the rectal stump staple line and engage with the anvil. This ensures that the stapler is suitably positioned to allow the dispensed staples to pass through both the distal stump and the colon that is attached to the anvil by way of, for example, a purse string suture.

The staples delivered by the stapling means can be arranged so as to provide a substantially circular arrangement. The arrangement of staples is referred to as the staple line. The staples may be positioned such that they are aligned with the circumference of the circular staple line. Alternatively, they may be aligned with the radius of the circular staple line, or at an angle between the radius and the circumference of the circle. Multiple rows of staples may be present, for example 2, 3, 4 or 5 rows of staples. In some embodiments the stapling device will be presented with the option of either two or three or more concentric rows of staples mounted circumferentially within the staple housing.

The trigger 112 can be in the form of, for example, a lever, as shown in FIG. 2. In such embodiments, activation of the trigger causes the stapling means to be activated by way of mechanical transfer of force or energy. Alternatively, the trigger may simply be a push button which causes the stapling means to be actuated automatically, for example by the use of electrically powered internal components.

The grip area and trigger of the stapler are preferably arranged such that when a user grasps the stapler by the grip area, the user can simultaneously activate the trigger. For example, as shown in FIG. 2, the trigger (which, in the embodiment shown in FIG. 2, is a lever) may be attached to the stapler at a central portion of the stapler and the grip area may extend towards the proximal end of the stapler.

Figure 7:
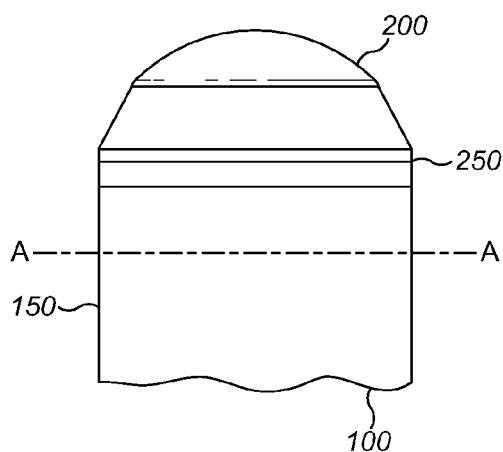
FIG. 7 shows a stapler apparatus according to the invention wherein the anvil 200 is fully engaged with the anvil docking pin 130 and the anvil docking pin is fully retracted into the stapler 100. The tissue or tissues being stapled would be disposed at the interface 250 between the anvil head 220 and stapling means 150.

In some embodiments, the distal end of the stapler also comprises a retracting means 114, as shown in FIG. 2. This retracting means can be rotated by the user and reversibly retracts the anvil docking pin (and anvil if engaged with the anvil docking pin) along the longitudinal axis of the stapler into the stapler body. If an anvil is engaged with the anvil docking pin, this causes the anvil head to move closer to the stapling means. FIG. 7 shows an anvil 200 fully engaged with a stapler 100 and fully retracted into the stapler. The components of the stapling apparatus are arranged such that the tissues to be stapled together are trapped between the anvil head and the stapling means. The tissues to be stapled together are trapped or secured at the interface 250 of the anvil 200 and stapling means 150. When the device is in use during surgery, the anvil head and stapling means will usually not come into direct contact with one another since there will be a layer or layers of tissue disposed between the two components at the interface 250 of the anvil head and stapling means.

The anvil docking pin (and anvil if engaged with the anvil docking pin) can be removed from the inside of the stapler by rotating the retracting means in the opposite direction. Alternatively, the anvil can simply be pulled off the anvil docking pin by the user.

In preferred embodiments, activation of the trigger is only performed after the retracting means has been rotated to move the anvil head closer to the stapling means and the tissues to be stapled together are trapped between the anvil head and the stapling means.

The retracting means can achieve the effect of guiding the anvil docking pin into the stapler along the longitudinal axis by any suitable means, for example a rod in the stapler body that couples the retracting means to the anvil docking pin, either directly or via intermediate components. The rod may have a screw thread that causes the anvil docking pin to be retracted into the stapler without causing the anvil docking pin to rotate. Other retraction mechanisms would be apparent to a person of skill in the art.

The retracting means may comprise flanges that extend outwards from the retracting means and/or grooves that are cut into the retracting means that allow the user to turn the retracting means more easily. The retracting means 114 as shown in FIG. 2 comprises grooves which make turning the retracting means easier for the user.

In the stapler of the invention, activation of the trigger causes the stapling means to be actuated. In some embodiments, the apparatus is arranged during use such that one surface to be stapled is connected to the anvil via the anvil head. The other surface to be stapled is positioned relative to the stapling means in such a way so as to allow actuation of the stapling means to connect both surfaces with staples. Preferably, the surfaces to be stapled are maintained at the interface 250 between the anvil head and the stapling means.

In some embodiments, the retracting means is absent and activation of the trigger causes both the anvil docking pin (and anvil if the anvil is engaged with the stapler) to move towards the proximal end of the stapler, and the stapling means to be actuated.

In some embodiments of the invention, the anvil head cross section in the transverse plane is substantially circular and the diameter differs according to the tissue being stapled. For example, the diameter of the anvil head may be in the range of 10 to 50 mm, more preferably in the range of 20 to 35 mm. In some embodiments, the diameter of the anvil head is 21, 25, 28 or 32 mm.

In certain embodiments, the anvil is equipped with colour markings that provide instant visual information to the user regarding the diameter of the anvil head. Generally, the diameter of the anvil head will correspond to the diameter of the stapling means such that the anvil head and the stapling means align when the anvil docking pin is retracted into the stapler. The stapler may also be equipped with corresponding colour markings that provide information to the user regarding the diameter of the stapler. The diameter of the stapling mean may be in the range of 10 to 50 mm, more preferably in the range of 20 to 35 mm. In some embodiments, the diameter of the stapling means is 21, 25, 28 or 32 mm.

In one embodiment of the invention, the stapler also comprises a safety catch (116), as shown in FIG. 2. This safety catch is moveable by the user and can be reversibly engaged. When the safety catch is engaged, it prevents the trigger from being activated by the user. Consequently, the safety catch can prevent the stapler from being actuated accidentally. When the safety catch is disengaged, the trigger can be fully activated and hence the stapling means can be actuated.

The stapling means comprises a stapler housing, a circular or cylindrical blade, a row of circumferentially arranged staple slots around the outside of the circular blade, and a driving blade. The circular blade and driving blade are moveable substantially parallel to the longitudinal axis of the stapler. The diameter of the stapling means usually refers to the diameter of the stapler housing.

The staple slots are provided with staples when the stapler apparatus is to be used. The staples for use in the stapler apparatus of the invention generally comprise a continuous piece of metal or plastic which is deformable. The continuous piece of metal or plastic is bent so as to form a crown and two sharp or pointed legs substantially perpendicular to the crown. The legs pierce the material being stapled. The length of these legs determines the height of the staple and can be varied according to the thicknesses of the tissues being stapled. Example leg lengths (and hence staple heights) include 2, 3, 4, 4.2, 5, 6, 7, 8, 9, 10, 15, 20, 25, 30, 35, 40 and 50 mm, preferably between 2 and 30 mm, or 3 and 20 mm, or 4 and 15 mm. When the staples are installed in the stapler, the legs point towards the distal end of the stapler.

The length of the crown can also vary, for example they crown may have a length of 2, 3, 3.8, 4, 5, 6, 7, 8, 9, 10, 11, 12, 13, 14 or 15 mm. Preferably, the length of the crown is between 3 and 15 mm or 3 and 10 mm. The length of the crown determines the distance of the legs from each other.

The staples can be made of any suitable material, for example titanium, titanium alloys (for example nitinol, also known as nickel titanium since it is an alloy of titanium and nickel) or stainless steel or other metal or plastics suitable for surgical purposes. Alternatively, biodegradable staples may be used, for example those made of mostly polylactic acid formulations.

The staples generally are initially formed into a "U" shape or similar shape prior to use, for example a rectangular or square shape wherein the staple forms three sides of the rectangle or square (for example, the legs are usually arranged substantially perpendicular to the crown).

As the trigger 112 of the stapler 100 is activated by a user, the circular blade and the staples are projected from the stapler housing. The staples are projected by the distally advancing driving blade, ejecting the staples along the longitudinal axis of the stapler and through any layers of tissue or material disposed at the interface 250 between the anvil head and the stapling means. The legs of the staples pierce the material or tissue being stapled. Once the staples have pierced the material, the legs are pressed against the anvil head so as to bend the staples inwards or outwards and hold the staples in place. The legs may be bent to the extent that they are now parallel or substantially parallel to the crown. When the legs are bent inwards, this forms a characteristic "B" shape common to many staples once used. The staples are deformed by pressing against the anvil such that they are flattened and the layers of tissue or material are held together by the flattened staples.

During actuation or firing of the stapling means, the circular blade, or trephine, advances along the longitudinal axis of the stapler to cut the tissue or material engaged with the stapler. A ring or disc of tissue is therefore excised by the stapler. The stapler apparatus is removed and a continuous lumen is established between the surfaces or tissues being stapled together. For example, this may cause a section of bowel to become reattached to another section of bowel or to a rectal stump whilst maintaining a hollow lumen through which faecal matter can pass. Alternatively, the circular blade may establish a stoma between an internal lumen (such as that inside the perineal cavity or GI tract) and the exterior of the body. The circular blade has a diameter that is smaller than the diameter of the driving blade and the arrangement of the staple slots such that only a section of tissue inside the staple line is excised. The staple line is left intact to hold the two surfaces together.

Stapling means that are suitable for use in the stapler apparatus of the invention are further described in U.S. Pat. Nos. 4,576,167 and 5,758,814, the contents of which are hereby incorporated by reference.

Additionally, when the device is in use, mesh reinforcement or other reinforcing material may be placed between the two layers of tissue that are being stapled together. Alternatively, or additionally, the mesh may be applied above or below the tissues being stapled. This mesh or other material serves to reinforce the anastomosis or stoma trephine being formed since the applied staples pass through both layers of tissue and the mesh. The mesh may also improve the seal between the two layers of tissue help to prevent leakage of any material from the lumen of the organ into the body cavity. Mesh reinforcement may also assist in preventing adverse consequences such as parastomal herniation.

The mesh can be made of any suitable material, such as a synthetic or a biological material. When operating the device the mesh or meshes may be placed on the anvil docking pin or the anvil shaft prior to actuation of the stapling means.

Generally the mesh is wider than the width of the anvil head and stapling means. This ensures the staples engage the mesh. The mesh can be any suitable configuration, for example circular, square, ovoid and so on. If the mesh is circular, then the mesh generally has a greater diameter than the anvil and/or the stapling means. Generally, the mesh is of a suitable size and shape to overlay the entire perimeter of the anastomosis or stoma trephine.

Synthetic materials suitable for the mesh include polypropylene, polyester and polytetrafluoroethylene (PTFE, for example compressed, expanded or electro spun). Polypropylene is stable, strong, inert and has good handling qualities. The polypropylene meshes are made up of polypropylene fibres arranged in a network with pores of different sizes. PTFE meshes are smooth, soft and strong and allow good tissue ingrowths.

Biological meshes include those harvested from cows, pigs and horses such as pericardium, but also other organs including dermis tissue.

Figure 8:
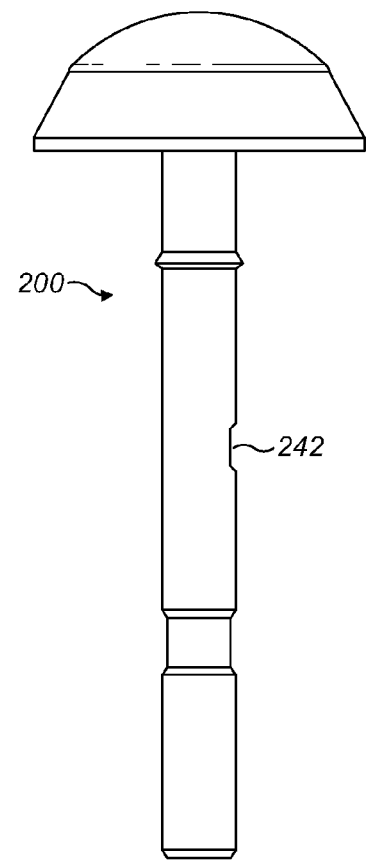
FIG. 8 shows an anvil of the invention 200 as shown in FIG. 4, but the anvil has been rotated 90°.

In one embodiment, the anvil shaft can comprise one or more circumferential indentations 242, as shown in FIGS. 4 and 8. These allow the anvil to be grasped more easily during surgery and provide greater dexterity and continuity of movement between the user and the anvil. Hence these indentations serve as gripping aids. The anvil shaft may comprise one or several indentations, example 2, 3, 4, 5, 6, 7, 8, 9, 10 or more indentations that provide this advantage. For example the anvil shaft may comprise 1 to 2, 1 to 3, 1 to 4, 1to 5, 1 to 6, 1 to 7, 1 to 8, 1 to 9 or 1 to 10 indentations. The indentations can extend completely around the circumference of the anvil shaft, for example to form annular grooves, or they may be restricted to one section of the circumference of the anvil shaft as shown in FIGS. 4 and 8. The indentations may be present in pairs such that they do not extend around the entire circumference of the anvil shaft but are aligned so that indentations are present on opposing sides of the anvil shaft. An anvil shaft may include 1, 2, 3, 4, 5, 6, 7, 8, 9 or 10 pairs or 1 to 2, 1 to 3, 1 to 4 or 1 to 5 pairs of opposing indentations.

Figure 6:
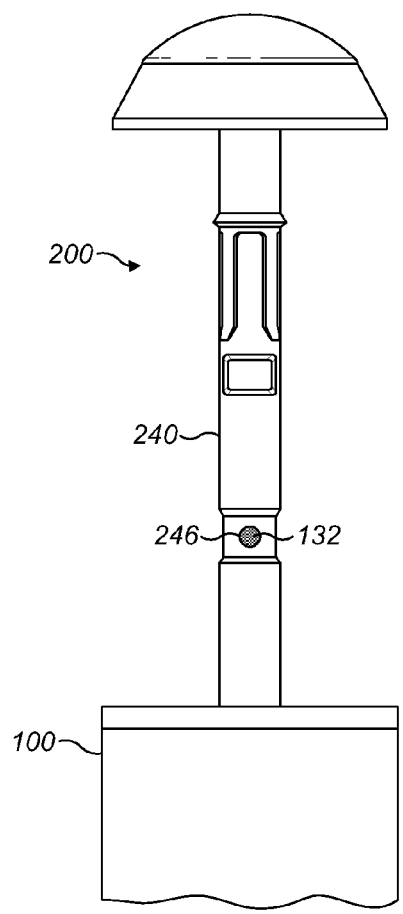
FIG. 6 shows a stapler apparatus according to the invention wherein the anvil 200 is fully engaged with the anvil docking pin 130.
Figure 13A:
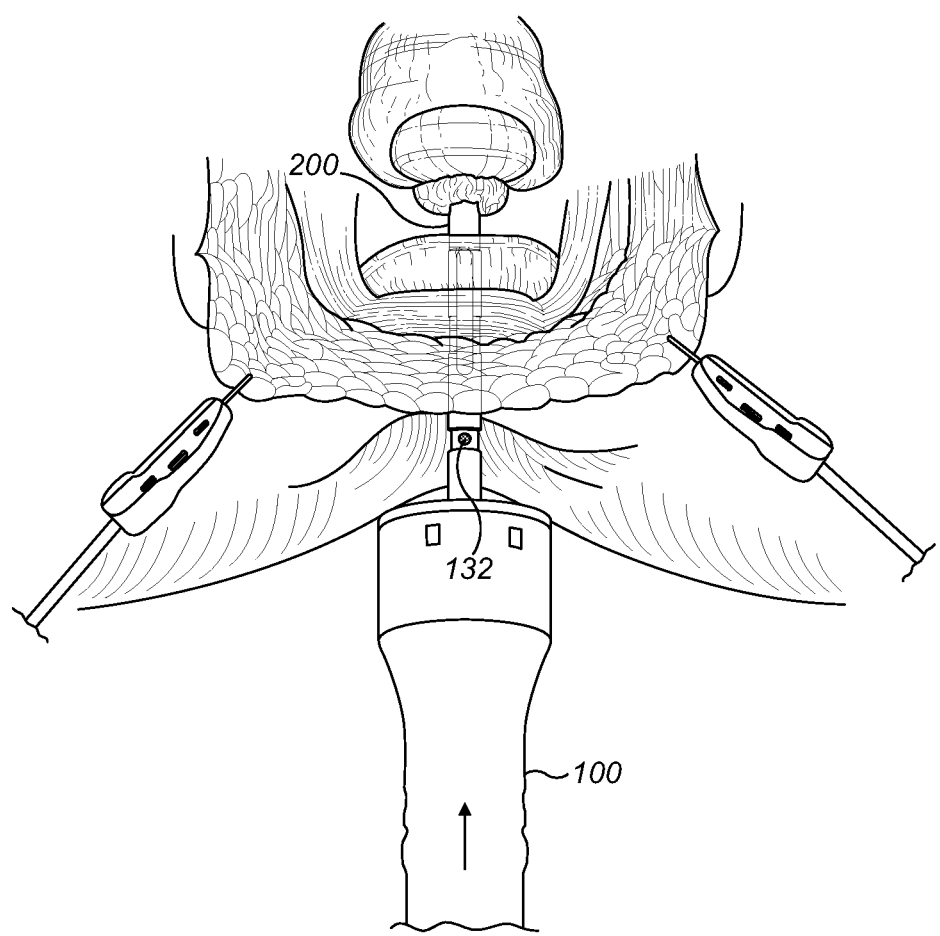
FIGS. 13a and 13b shows the anvil 200 and stapler 100 fully docked. An anvil docking indicator 132 is visible through a viewing window present on the anvil shaft.

In a further embodiment, as shown in FIG. 4 the anvil shaft 240 can comprise a viewing window 246. The anvil docking pin 130 can also comprise a docking indicator 132 such that when the anvil 200 is fully docked over the anvil docking pin 130, the docking indicator 132 is visible through the viewing window 246. FIGS. 6 and 13*a* show the anvil fully engaged with the anvil docking pin and the docking indicator 132 is visible through the viewing window 246.

This viewing window provides information to the user as to the extent to which the anvil is engaged with the stapler. The viewing window and docking indicator are positioned such that when the anvil is fully engaged with the stapler, only then is the docking indicator visible to the user through the viewing window. The combination of a viewing window, a docking indicator and the elongated anvil shaft provides an advantage over the prior art since endo-anal and extracorporeal docking is facilitated by the presence of an elongated shaft, and hence the viewing window and docking indicator are visible to the surgeon or other user when the stapler apparatus is being used.

The docking indicator can be a marking such that it is visually distinguishable from the rest of the anvil docking pin. For example, the docking indicator may be a section of the anvil docking pin that is coloured (for example red) to allow a quick visual confirmation that the anvil is fully engaged with the stapler. The docking indicator may extend around the entire circumference of the anvil docking pin such that the docking indicator is visible through the viewing window regardless of the relative rotational orientations of the anvil and anvil docking pin. The docking indicator is positioned on the anvil docking pin such that the docking indicator aligns with the viewing window only when the anvil is fully docked onto the anvil docking pin.

The anvil shaft 240 may include one viewing window (as shown in FIGS. 4 and 8; in FIG. 8, the anvil has been rotated 90° and hence the viewing window is no longer visible). Alternatively, the anvil shaft may include a plurality of viewing windows, for example 2, 3, 4, 5, 6, 7, 8, 9 or 10 or more, which allow the docking indicator to be seen when the anvil shaft is fully engaged with the anvil docking pin. The anvil shaft may therefore include 1 to 2, 1 to 3, 1 to 4, 1 to 5, 1 to 6, 1 to 7, 1 to 8, 1 to 9 or 1 to 10 viewing windows. Alternatively still, the anvil shaft may include a section made of a transparent or semi-transparent material that allows the docking indicator to be seen when the anvil shaft is fully engaged with the anvil docking pin. References to "viewing window" therefore include such transparent or semi-transparent sections of the anvil shaft as well as actual holes or apertures in the side of the anvil shaft.

Figure 24:
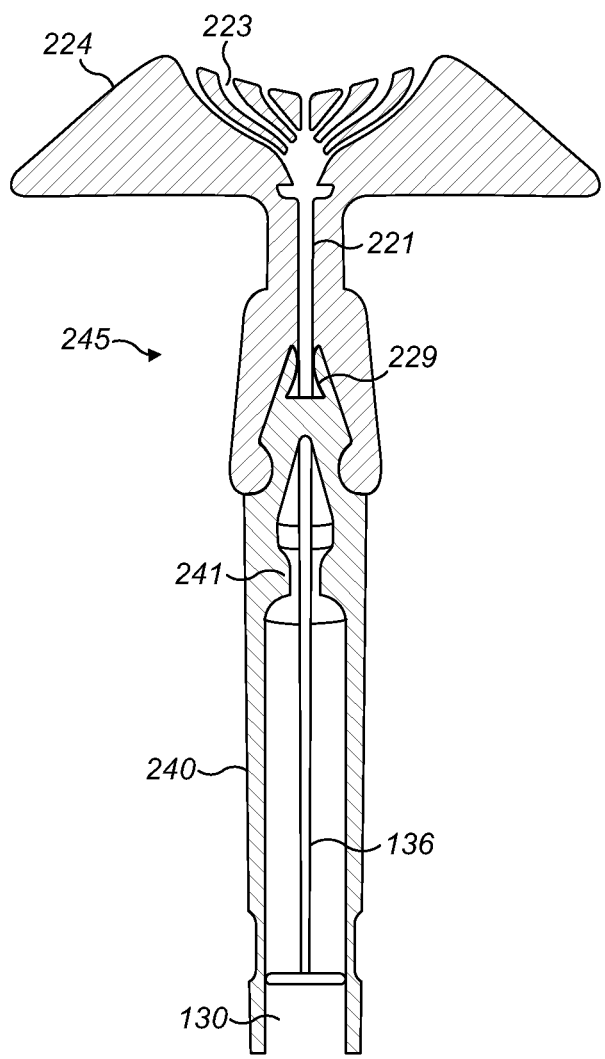
FIG. 24 shows an anvil 245 of the invention comprising a network of channels 221 docked onto an anvil docking pin 130 of a stapler apparatus of the invention.

In one embodiment, since the anvil docking pin is insertable into the anvil shaft, the anvil docking pin further comprises a retaining means 134 that reversibly secures the anvil in position when the anvil is fully docked on the anvil docking pin. The anvil shaft therefore comprises an internal chamber 241 which is adapted to receive an anvil docking pin. FIG. 4 shows an anvil of the invention 200 aligned ready for docking onto the anvil docking pin 130. FIG. 24 is a cross-sectional view showing the anvil docking pin 130 inserted into the internal chamber 241 of an anvil shaft 240.

This retaining means may take the form of a narrowing and widening of the anvil docking pin in conjunction with a narrowing of the internal chamber the anvil shaft. The internal chamber of the anvil shaft is adapted to complement the shape of the anvil docking pin such that when the anvil is fully engaged with the anvil docking pin, the narrowing of the internal chamber of the anvil shaft is aligned with the narrowing of anvil docking pin, thereby causing the anvil to be removably secured in place.

As shown in FIG. 4, the retaining means may comprise an outer retaining means 248 present on the anvil shaft and an inner retaining means 134 present on the anvil docking pin.

The outer retaining means can be a section of the anvil shaft that can reversibly extend beyond the circumference of the anvil shaft when a force externalizing radially from the centre of the anvil shaft is applied to the outer retaining means. The outer retaining means also corresponds to a narrowing of the inner chamber of the anvil shaft. For example, when the inner retaining means 134 comprises a narrowing and a widening of the anvil docking pin (as shown in FIG. 4) and the anvil docking pin is docked into the anvil shaft, the narrowing of the internal chamber 241 of the anvil shaft 240 causes the retaining means 248 of the anvil shaft 240 to be pushed outwards. When the inner retaining means 134 is pushed past the narrowing of the inner chamber 241 of the anvil shaft present at the outer retaining means 248, the outer retaining means returns to its original position in line with the sides of the anvil shaft 240. The narrowing of the inner chamber 241 of the anvil shaft 240 at the outer retaining means 248 corresponds to the narrowing of the diameter of the anvil docking pin 130 at the inner retaining means 134, thereby causing the anvil to be removably secured in place.

Such retaining means are sometimes referred to as a spring click docking mechanisms. Other retaining means would be apparent to a person of skill in the art.

In addition to reversibly securing the anvil in place, the presence of a retaining means also has the added advantage that an audible sound is emitted as the anvil is engaged with the stapler, providing auditory confirmation to the user that the anvil is fully engaged with the stapler.

The retaining means also allows the stapler apparatus to be manipulated without the anvil becoming detached from the stapler. Hence the retaining means is an advantageous safety feature of the stapler.

Preferably, the anvil head has a circular cross section in the transverse plane. The anvil head comprises two opposing surfaces 222 and 224. The anvil shaft extends outwards from the centre of one of these surfaces and is perpendicular or substantially perpendicular to the plane of the surface from which the docking pin extends. The anvil shaft is therefore connected to or integral with the anvil head at one end of the anvil shaft. In some embodiments, the anvil head comprises a flat planar surface from which the anvil shaft extends. The opposing surface may be curved, conical or frustoconical in shape. Generally the anvil head is shaped to provide an atraumatic top to the anvil when it is manipulated, either via an enterotomy (a surgical incision into the intestine) or via the natural passageways in hollow organs such as stomach, bowel, oesophagus or other hollow organs.

Alternatively, one of the opposing surfaces 222 or 224 may be concave and the other convex, the two opposing surfaces being complementary to each other and the anvil head having a thickness determined by the distance between the two opposing surfaces. In this embodiment, the anvil shaft extends from the centre of the concave surface 222. Generally, at least part of the concave surface is flat and is aligned perpendicular to the longitudinal axis of the stapler when the anvil shaft is engaged with the anvil docking pin.

The surface of the anvil head 222 from which the anvil shaft extends generally includes a series of indentations or pockets that align with the staples slots of the stapling means 150 when the anvil is engaged with the anvil docking pin and the anvil docking pin is retracted into the stapler. These indentations cause the staples to bend inwards or outwards as the stapling means is actuated. Consequently, once the staple legs pass through the tissues being stapled and are bent inwards or outwards by the anvil, the staples are secured in place and the two tissues are fixed together (such as two hollow organs when creating an anastomosis or in the creation of a stapled stoma trephine during stoma creation). The indentations in the surface of the anvil head 222 can be formed by, for example, mechanical pressing or engraving.

In one embodiment of the invention, in addition to the internal chamber 241 that is adapted to receive the anvil docking pin, the anvil shaft includes a central hollow channel 221, as shown in FIG. 24. This central hollow channel may extend from the internal chamber 241 of the anvil shaft 240 through the entire thickness of the anvil head 220 and terminate in an aperture 223 in the surface 224 of the anvil head 220. The anvil shaft may include a plurality of these channels, each terminating in separate apertures in the surface 224 of the anvil head. Alternatively, the anvil 245 may comprise one hollow channel 221 in the anvil shaft that branches out into a plurality or network of channels in the anvil head, each ending in an aperture in the surface 224 of the anvil head. FIG. 24 shows an anvil 245 according to this embodiment of the invention, wherein the anvil comprises a central hollow channel 221 branching out into a plurality of channels each ending in an aperture 223 in the surface 224 of the anvil head 220.

These channels allow air to be drawn through the anvil head when the anvil 245 is attached to a suction device 225. When suction is applied through the anvil, the anvil can be used to manipulate biological tissue or other substances by causing the tissue to become reversibly attached to the anvil head by the use of suction through the channels. The suction causes a vacuum that facilitates reversible attachment of tissue to the anvil head. The suction can be removed when the tissue is in an appropriate place or is accessible using, for example, forceps or other surgical device or a surgeon's fingers.

The suction device can have a fitting 227 that is adapted to allow the fitting to engage with the anvil shaft in the same manner as an anvil docking pin. The anvil 245 may include a seal 229 which provides an air-tight seal between the suction device and the anvil channels. The seal may be positioned where the plurality of channels inside the anvil head converge into one channel, or may be positioned further down the anvil shaft to where the fitting of the suction device terminates when the suction device is engaged with the anvil.

Figure 25:
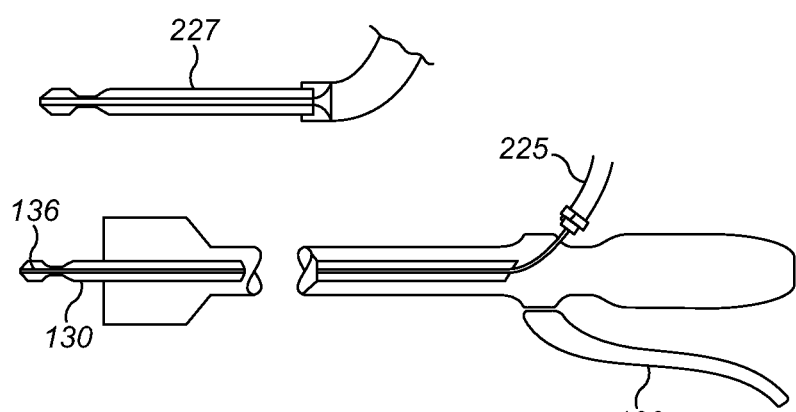
FIG. 25 shows a suction device fitting 227 and a stapler of the invention 100 attached to a suction device 225.

Optionally, the anvil docking pin 130 can also be equipped with one or more hollow channels 136, as shown in FIG. 24. The hollow channels allow air to be sucked through the anvil docking pin and then through a channel (or channels) 221 and aperture (or apertures) 223 in the anvil head 220. Consequently, when the anvil is engaged with the anvil docking pin, the stapler can be attached to the suction device and tissue can be manipulated even when the anvil is engaged with the stapler. This is shown in FIG. 25. A stapler of the invention 100 is attached to a suction device 225 which draws air through the anvil docking pin 130 by means of a central channel 136 in the anvil docking pin 130.

Figure 26:
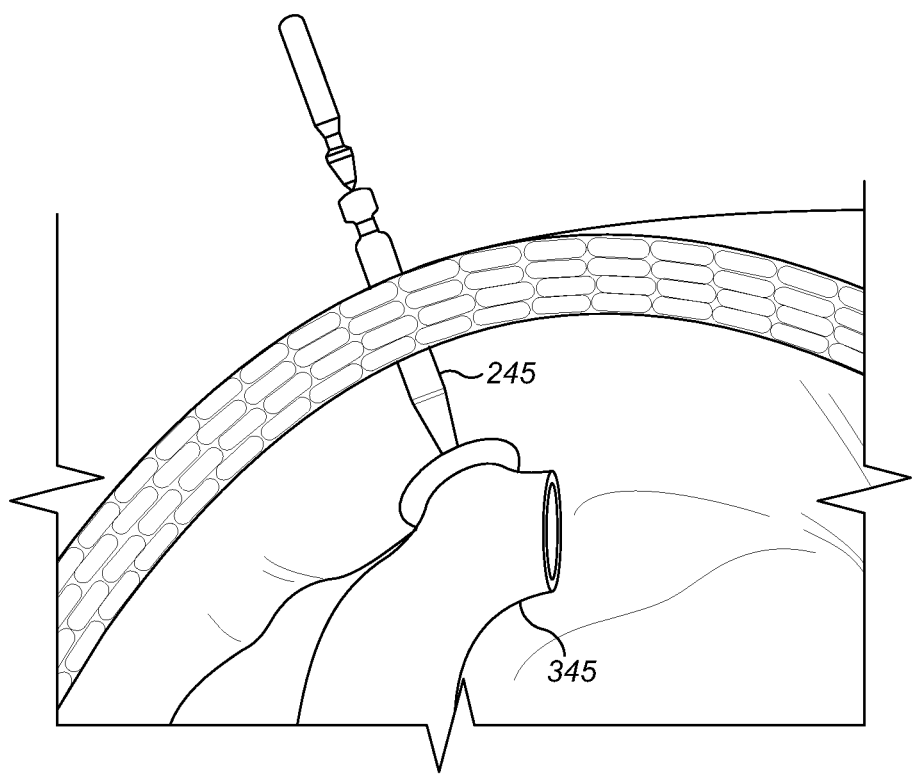
FIG. 26 shows a section of bowel 345 being manipulated by an anvil 245 when attached to a suction device.

Preferably, in these embodiments including one or more channels in the anvil head, the suction device is controllable so the amount of suction applied to the tissue can be varied and hence damage to the tissue can be prevented (atraumatic manipulation of the tissue). Manipulation of the tissue includes movement and removal of tissues and organs within the human body during a variety of surgical procedures, for example atraumatic fixation and retraction of bowel in the creation of stapled stomas, particularly to ensure the correct orientation of the bowel as it is exteriorized to form the stoma. Manipulation of a section of bowel is shown in FIG. 26.

In one embodiment there is provided a stapler apparatus of the invention, further comprising a gauge on the body of the stapler that provides information to the user as to how far the anvil docking pin has been retracted into the stapler. As the user turns the retracting means, the gauge moves up and down according to how far inside the stapler the anvil docking pin has been retracted. This gauge may include certain upper and lower limits. Below the lower limit, the anvil docking pin has not been refracted sufficiently enough to allow the staples to be bent by the indentations in the anvil head to secure them in place. Above the upper limit, the anvil docking pin has been retracted so far that damage could be caused to the two tissues disposed at the interface between the anvil head and the stapling means.

In preferred embodiments, the gauge is present on the distal end of the stapler such that when the stapler is grasped by the user, the user's hand does not obscure the gauge from view.

The stapler and stapler body of the invention can be made of any suitable materials known to a person of skill in the art. For example, the stapler may include plastics (such as polyamide, polystyrene, polyvinyl chloride, polypropylene, polyurethanes, polycarbonates or polyetheretherketone), metals (such as stainless steel or titanium) or porcelain. The anvil may also be made of any of these materials.

In a second aspect of the invention, there is provided an anvil 200 for a stapler apparatus comprising an anvil head 220 and an anvil shaft 240, characterised in that the length of the anvil shaft is at least 4 cm.

The anvil shaft is adapted to receive an anvil docking pin to allow engagement with a surgical stapler. The surgical stapler is suitable for forming an anastomosis and is generally an intraluminal circular stapler.

In a third aspect of the invention, there is provided the use of the stapler apparatus or anvil of the invention in the formation of an anastomosis or stoma trephine.

The anastomosis or stoma trephine may be formed in any desirable surface or biological tissue in a patient or subject that is capable of being stapled. Suitable biological tissues include organ walls, the endoderm, ectoderm, mesoderm, the alimentary canal, small intestine, large intestine, duodenum, jejunum, ileum, cecum, colon, rectum, connective tissue, muscle tissue, epithelial tissue, stomach, oesophagus, trachea, peritoneum, rectus sheath, distal rectal stump, endothelium, gut endothelium, skin and the abdominal wall. Anastomoses or stoma trephines may be formed between two or more of theses biological tissues. For anastomoses, both tissues generally have lumens which are joined together in forming the anastomosis. For example, an anastomosis may be formed between two pieces of bowel or between the intestine and a distal rectal stump of a patient. Such anastomoses are know as end-to-end anastomoses. The stoma trephine may be formed in the abdomen of a patient or in any desired place where a stoma trephine is to be formed.

In a fourth aspect of the invention, there is provided a method of forming or creating an anastomosis between two surfaces or tissues using the stapler apparatus of the invention, comprising attaching a first surface or tissue to be stapled to the anvil 200 of the stapler apparatus, engaging the anvil docking pin 130 with the anvil shaft 240, positioning the stapler 100 to engage the stapling means 150 with a second surface or tissue to be stapled and activating the trigger 112 to connect together the first and second surfaces or tissues with staples. The method can be said to be forming an anastomosis between the lumen of the first and second surfaces or tissues and can be an end-to-end anastomosis. The lumen may be the gut lumen, depending on the location of the anastomosis.

In one embodiment of the invention, the method of forming an anastomosis further comprises the step of retrieving the anvil shaft through the staple line of the second surface. The method may also comprise operating a retracting means to retract the anvil docking pin into the stapler. The anvil may be attached to the first surface (for example a section of bowel or intestine) by way of a purse string suture or by any suitable means know to a person of skill in the art.

In such embodiments where a purse string suture is used, the first tissue is closed around the anvil shaft with a purse string suture and the anvil head is therefore enclosed in the lumen of the first tissue. The anvil shaft passes through the purse string suture and is exposed ready for docking onto the anvil docking pin. Materials used for creating the sutures include polydioxanone (PDS), polyglycolic acid, polylactic acid, nylon and polypropylene.

The anvil shaft may be manipulated using forceps. The forceps can be used to retrieve the anvil shaft past the staple line in the second surface such that the first surface is guided towards and past the staple line of the second surface. The staple line refers to the desired position of the staples after actuation of the stapling means.

In some embodiments, the second tissue may be punctured using the anvil docking pin of the stapler. Such an anvil docking pin comprises a trocar tip, which is suitable for puncturing the second surface. The second surface is punctured approximately at the centre of the circular staple line (or other suitably shaped staple line, depending on the arrangement of staples being used). If the second surface comprises a hole or incision around which is positioned the staple line, the method may further comprise closing this hole using sutures or staples and then puncturing the staple line with a trocar-tipped surgical stapler of the invention. For example, when creating an anastomosis between a section of bowel and a distal rectal stump, the distal rectal stump may be closed off or resected using sutures or staples prior to being pierced by a trocar-tipped stapler or other instrument. Alternatively, an incision may be created in the distal stump (or other tissue) in the centre of the staple line, allowing the anvil to be grasped and retrieved through the incision. This ensures correct positioning of the two surfaces (the piece of intestine and the distal rectal stump) at the interface between the anvil head and the stapling means to allow the staples to pass through both surfaces when the stapling means is actuated.

Once the trocar-tipped anvil docking pin has punctured the second surface, or once the anvil shaft has been retrieved through the staple line of the second surface, the anvil can be docked onto the stapler. The retracting means is optionally operated (as required) and the trigger is then activated. The stapling means is therefore actuated and the two surfaces are fixed together with staples. The circular blade of the stapling means also ensures a continuous lumen between the lumen of the first and second tissues.

Mesh reinforcement may be provided on the anvil shaft or anvil docking pin such that the mesh is also stapled to the anastomosis. The mesh may be positioned between the two surfaces or tissues being stapled. Alternatively, the mesh may be present above or below the surface being stapled. In some embodiments, one or more meshes may be used, for example 2, 3, 4 or 5 or more may be used.

If a mesh or meshes are used, the circular blade of the stapler apparatus will cut the mesh to ensure a continuous lumen between the two surfaces. Suturing of the outer rim of the mesh or meshes may be required to fully secure the meshes in position.

The step of positioning the stapler may include engaging the first and second surface with the interface 250 between the anvil head and the stapling means. The first and second surfaces are trapped or disposed between the surface 222 of the anvil head and the stapling means 150 such that when the stapling means 150 is actuated by activating the trigger 112, the legs of the staples pierces the surfaces and hold them together with staples. Advancement of the circular blade along the longitudinal axis causes a continuous lumen to be established between the two surfaces or tissues.

The stapler of the invention is depicted in use for creating an anastomosis in a bowel close to the anal verge in FIGS. 10 to 13.

Figure 10:
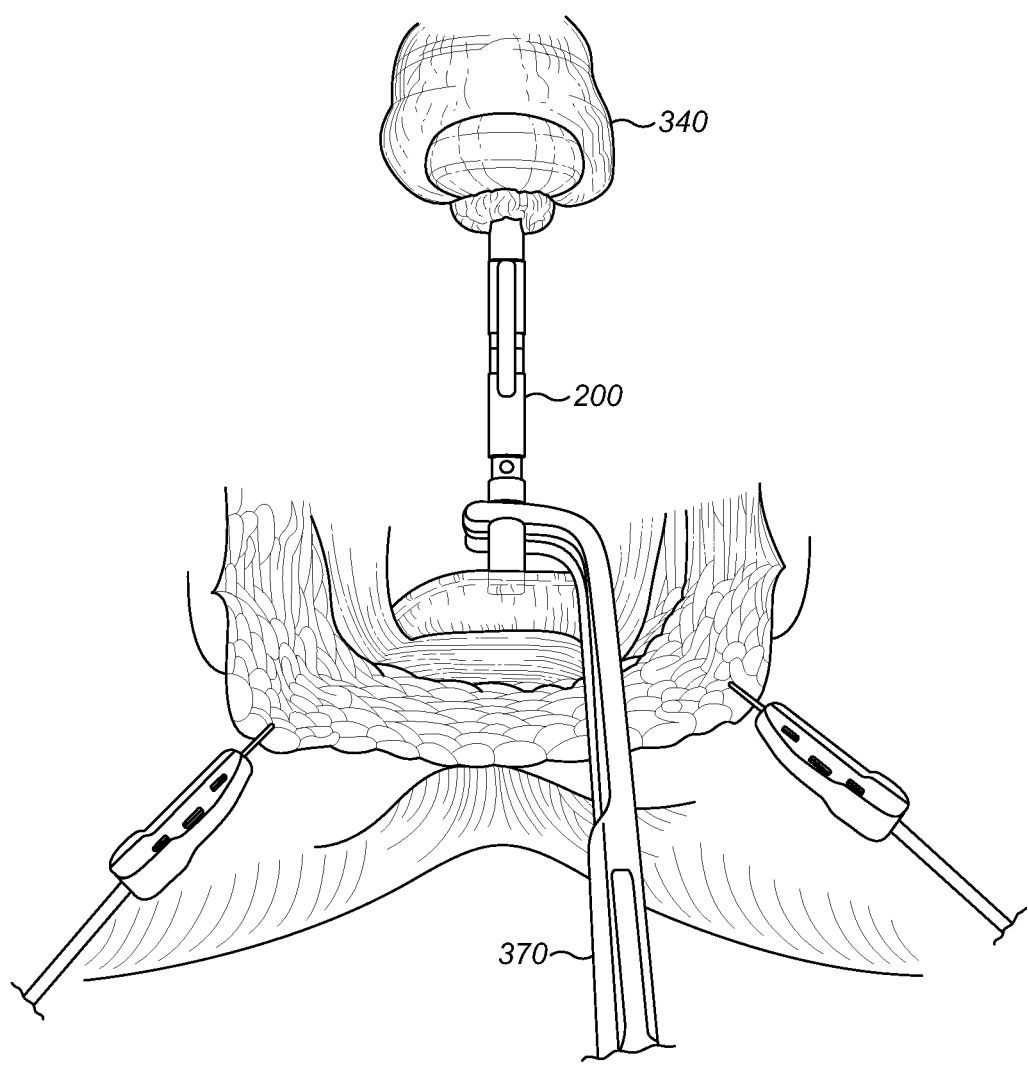
FIG. 10 shows the anvil of the invention 200 attached to a section of intestine 340 by a purse string suture in position immediately prior to docking procedure. The anvil is manipulated using tongs 370.

FIG. 10 shows the extended anvil of the invention in position immediately prior to the docking procedure. The anvil has been placed via purse string attachment within the proximal bowel which has been drawn into the perineal cavity by the use of specially modified anvil tongs 370 whose angle of attachment has been tailored to allow grasping of the anvil shaft parallel to the longitudinal axis of the stapler. The anvil shaft is grasped at one of the indentations or pairs of indentations 242 positioned along the anvil shaft. Alternatively, standard forceps can be used. The anvil shaft is positioned above the remaining distal rectal stump 350 that was previously resected with a linear stapling device or sutures.

Consequently, this invention further extends to tongs 370, comprising two elongate members attached to each other at or towards one end by a flexible join (for example a hinge or a pivot), the elongate members being curved at the other end. The curved section of the elongate members may be orientated at between 45° and 135° relative to the non-curved section of the elongate members (for example 90°). The elongate members are usually symmetrical in shape to one another. The curved ends of the elongate members comprise one or more curved recesses, wherein recesses in opposing elongate members are aligned with one another. This alignment may result in apertures in the tongs when the tongs are closed by a user, each aperture being defined by the aligned recesses in opposing elongate members. The recesses are adapted to receive the anvil shaft of the stapler apparatus of the invention and reversibly secure the anvil when the tongs are closed. More preferably, the tongs are used to grasp the anvil shaft by the indentation or indentations 242 present in one anvil shafts of the invention. Preferably, the curvature of the curved section of the elongate members allows grasping of the anvil parallel to the longitudinal axis of the stapler.

The adapted tongs provide greater dexterity to the surgeon when manipulating the anvil during a surgical procedure. The tongs may be used in such steps as the engaging and positioning steps outlined above.

Figure 11:
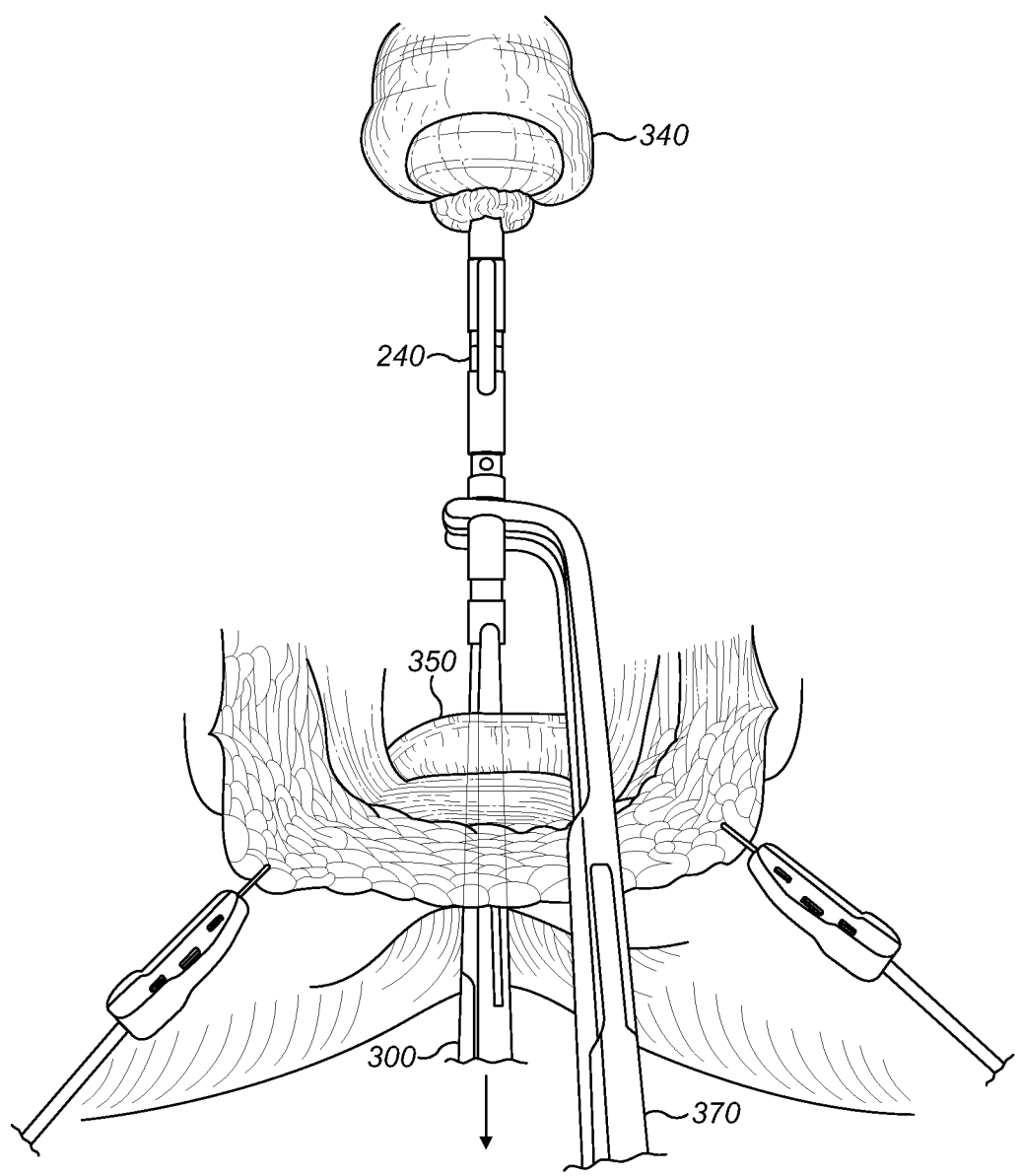
FIG. 11 shows grasping forceps 300 to secure, retrieve and draw the anvil shaft 240 through an enterotomy created in the distal rectal stump 350.

FIG. 11 shows the distal rectal stump staple line traversed by forceps 300 to secure, retrieve and draw the anvil shaft through the enterotomy created in the distal stump.

Figure 12A:
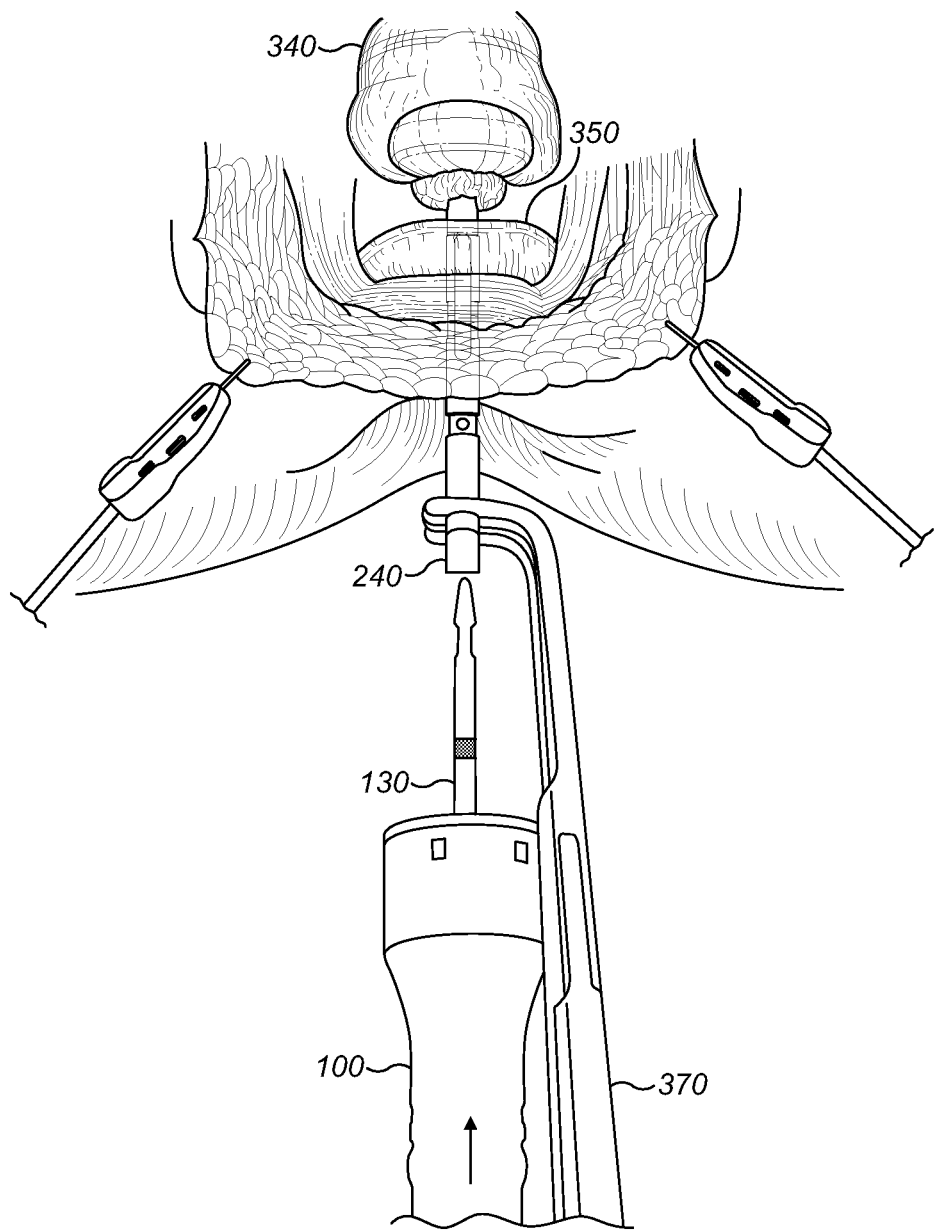
FIGS. 12a and 12b show the anvil shaft 240 fully retrieved through the distal stump 350 and fully externalised in preparation for endo-anal or extracorporeal docking of the anvil shaft 240 and anvil docking pin 130.
Figure 12B:
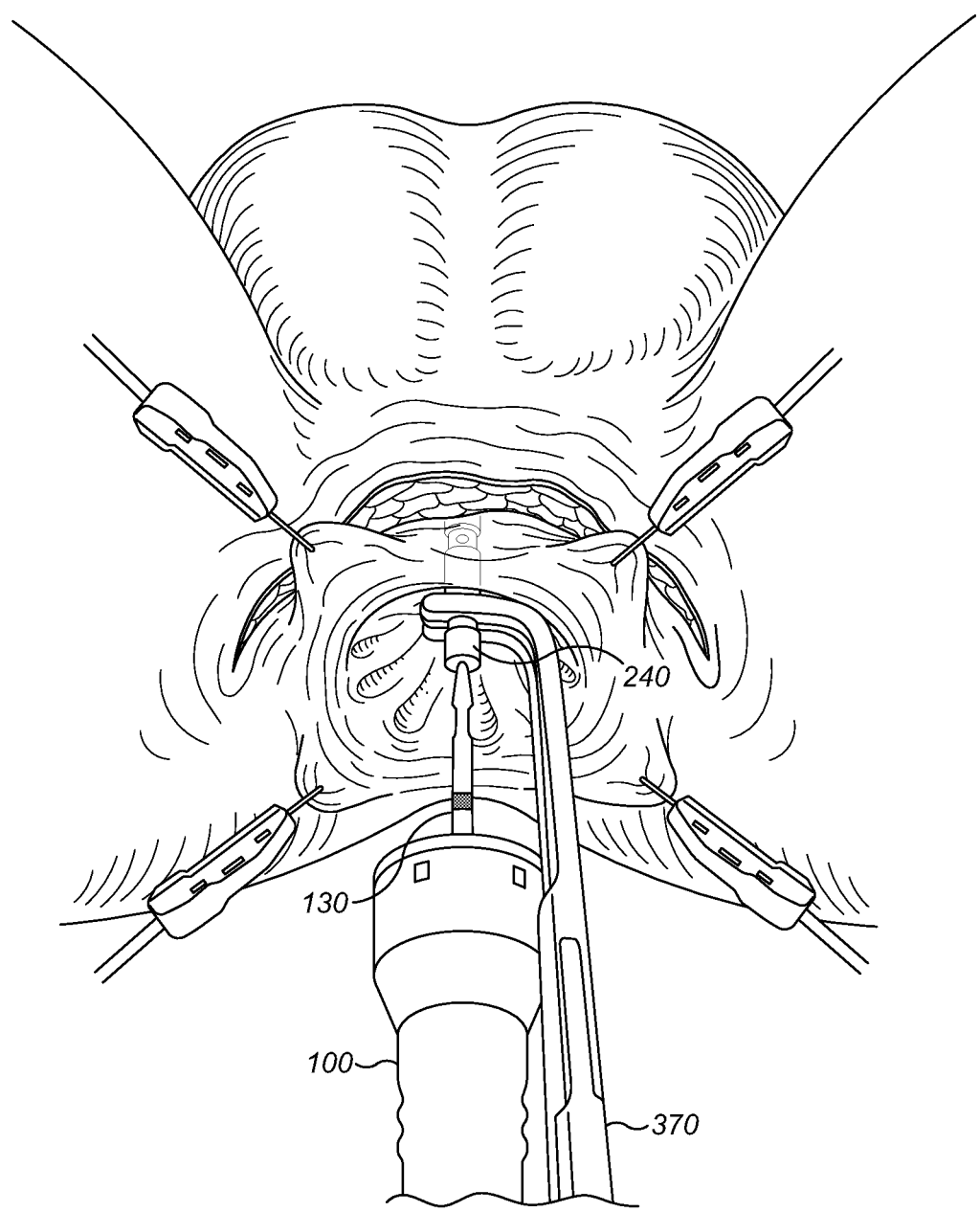

FIGS. 12a and 12b show the anvil fully retrieved through the distal stump enterotomy and fully externalised in preparation for endo-anal or extracorporeal docking of the anvil shaft and stapler. The anvil tongs 370 have been repositioned to grasp the anvil to stabilise and facilitate docking. FIGS. 12a and 12b clearly show the docking indicator on the anvil docking pin and the viewing window on the anvil shaft through which the docking indicator will be visible to confirm docking has been completed.

Figure 13B:
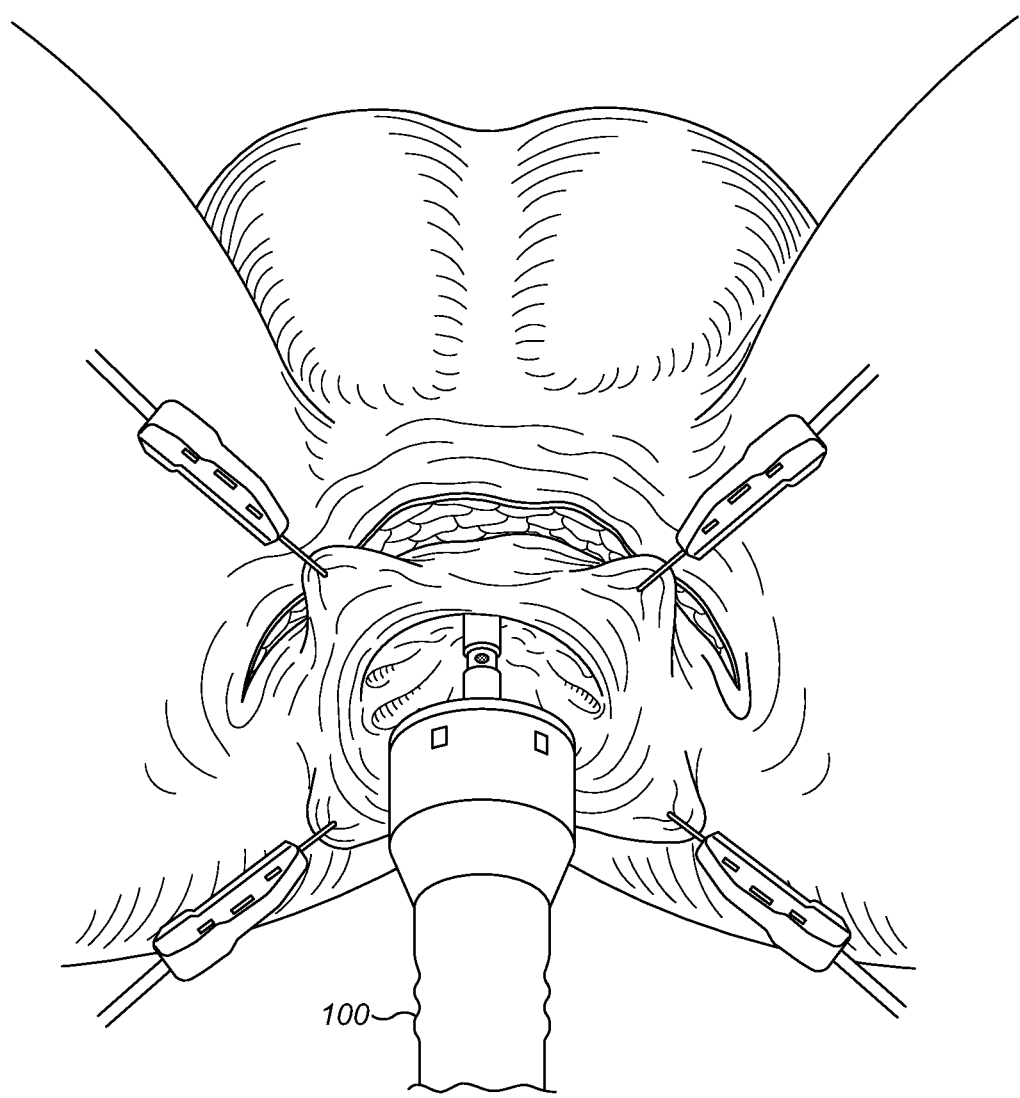

FIGS. 13a and 13b shows the anvil and anvil docking pin fully docked with the docking indicator clearly in view through the viewing window. The stapler device is then closed by activation of the trigger to draw the two tissues together such that the staple body housing passes endoanally into the anorectal stump, taking care to traverse the sphincter mechanism and the full length of the anorectal stump 350. When the anvil and stapler are suitably positioned, the stapling means is actuated to create the anastomosis.

The unique feature and design of the device of the invention allows for virtually unlimited extension of the anvil docking pin-anvil shaft assembly to allow for anatomical variances, such as obese patients, and for additional procedures, for example bariatric surgery procedures where externalisation of coupling of staple anvil assembly to stapler is desirable.

In a fifth aspect of the invention, there is provided a method of forming or creating a stoma trephine in a subject using the stapler apparatus of the invention, comprising:

forming an incision in a tissue where a stoma is to be formed;

positioning the anvil 200 of the stapler apparatus such that the anvil 220 head is inside the subject and the anvil shaft 240 is projecting through the incision;

docking the anvil shaft 240 onto the anvil docking pin 130 of the stapler 100; and activating the trigger 112 to dispense a series of staples in the tissue being stapled.

In some embodiments, the method of forming a stoma may additionally comprise the step of retrieving the anvil shaft through the incision, for example using forceps. The forceps may be used to manipulate the anvil shaft to manoeuvre the anvil shaft past the staple line in the tissue where the stoma trephine is to be formed. The anvil head may be attached to an organ or surface or tissue, for example a section of intestine or skin, such that the anvil head is contained within the lumen of the organ and the anvil shaft projects out of the tissue. The anvil shaft is then ready for engagement with an anvil docking pin. Therefore, methods of the invention can include the step of attaching the anvil via the anvil head to an organ, for example by means of a purse string suture.

In another embodiment of the invention, the method may comprise applying one or more mesh reinforcements to the anvil docking pin or anvil shaft.

As for the method of forming an anastomoses, the mesh or meshes may be arranged in any order, so that they are above or below the tissue being stapled or, where a plurality of tissues layers are being stapled together, the meshes may be positioned between the tissue layers. If a mesh or meshes are used, the circular blade of the stapler apparatus will cut the mesh to ensure a continuous lumen between the interior of the organ in which the stoma trephine is being formed and the exterior of the organ. Suturing of the outer rim of the mesh or meshes may be required to fully secure the meshes in position.

In yet another embodiment of the invention, the method of forming a stoma trephine may further comprise the step of operating the retracting means of the stapler to retract the anvil docking pin and engaged anvil into the stapler.

Manipulation or positioning of the anvil during the procedure may involve the use of forceps or the tongs 370, or both.

Actuation of the stapling means by activation of the trigger causes the staples to be dispensed and to fix together the tissue disposed at the interface between the anvil head and stapling means. Advancement of the circular blade along the longitudinal axis causes formation of the trephine between, for example, an internal cavity (such as the abdominal cavity) and the exterior of the body. The dispensed deformed staples secure the perimeter of the trephine by securing together layers of tissue.

The stapler of the invention is depicted in use for creating a stoma trephine in FIGS. 14 to 23.

Figure 14:
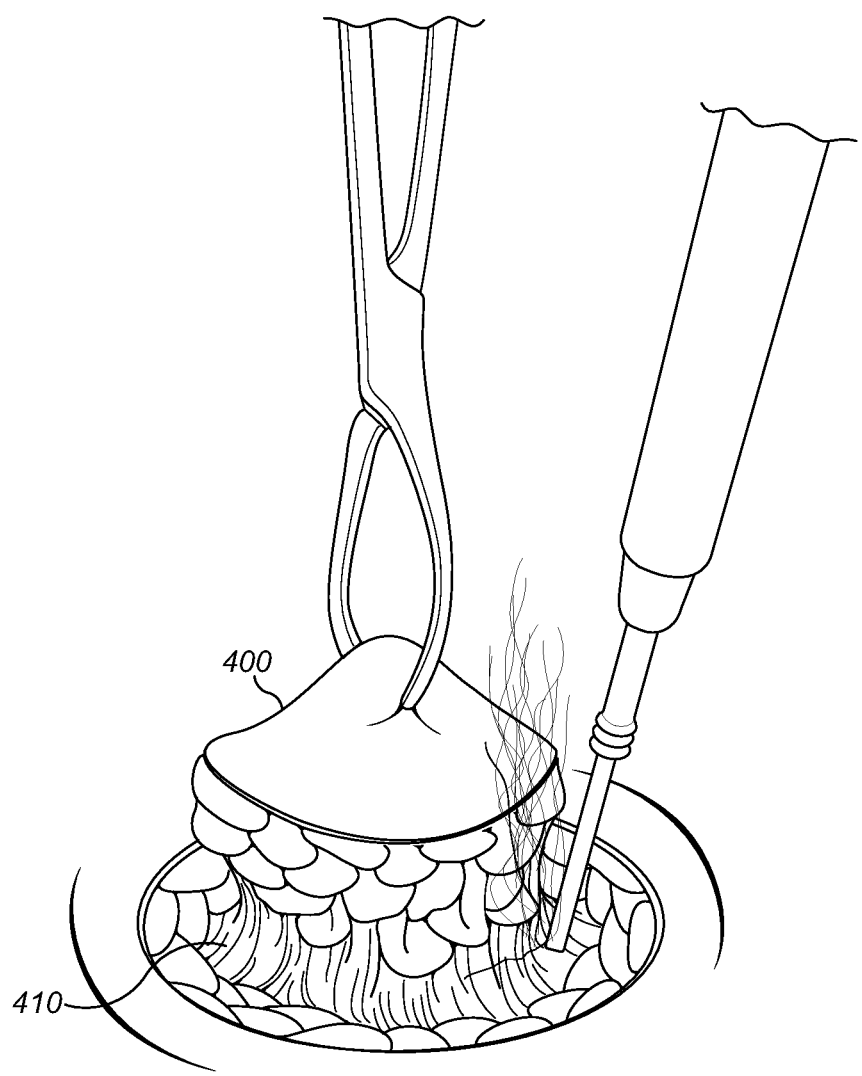
FIG. 14 shows the excision of a cylinder of abdominal wall skin and subcutaneous tissue 400 down to the rectus sheath 410 at the site at which a stoma trephine is to be formed.
Figure 15:
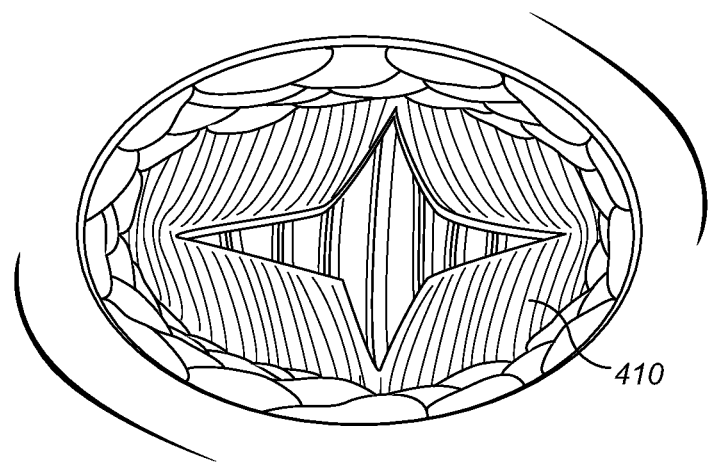
FIG. 15 show the rectus sheath 410 opened with a cruciate incision.

Formation of stomas (and stoma trephines) in open surgery generally commence by excising a cylinder of abdominal wall skin and subcutaneous tissue 400 down to the rectus sheath 410, as shown in FIG. 14. The sheath 410 is then opened with a cruciate incision and the rectus muscle split in the line of its fibres (FIG. 15). An anvil 200 of an appropriate size is then introduced via the open abdomen. The diameter of the stapler and anvil depends on the diameter of the bowel which will eventually traverse the stoma trephine.

Figure 17:
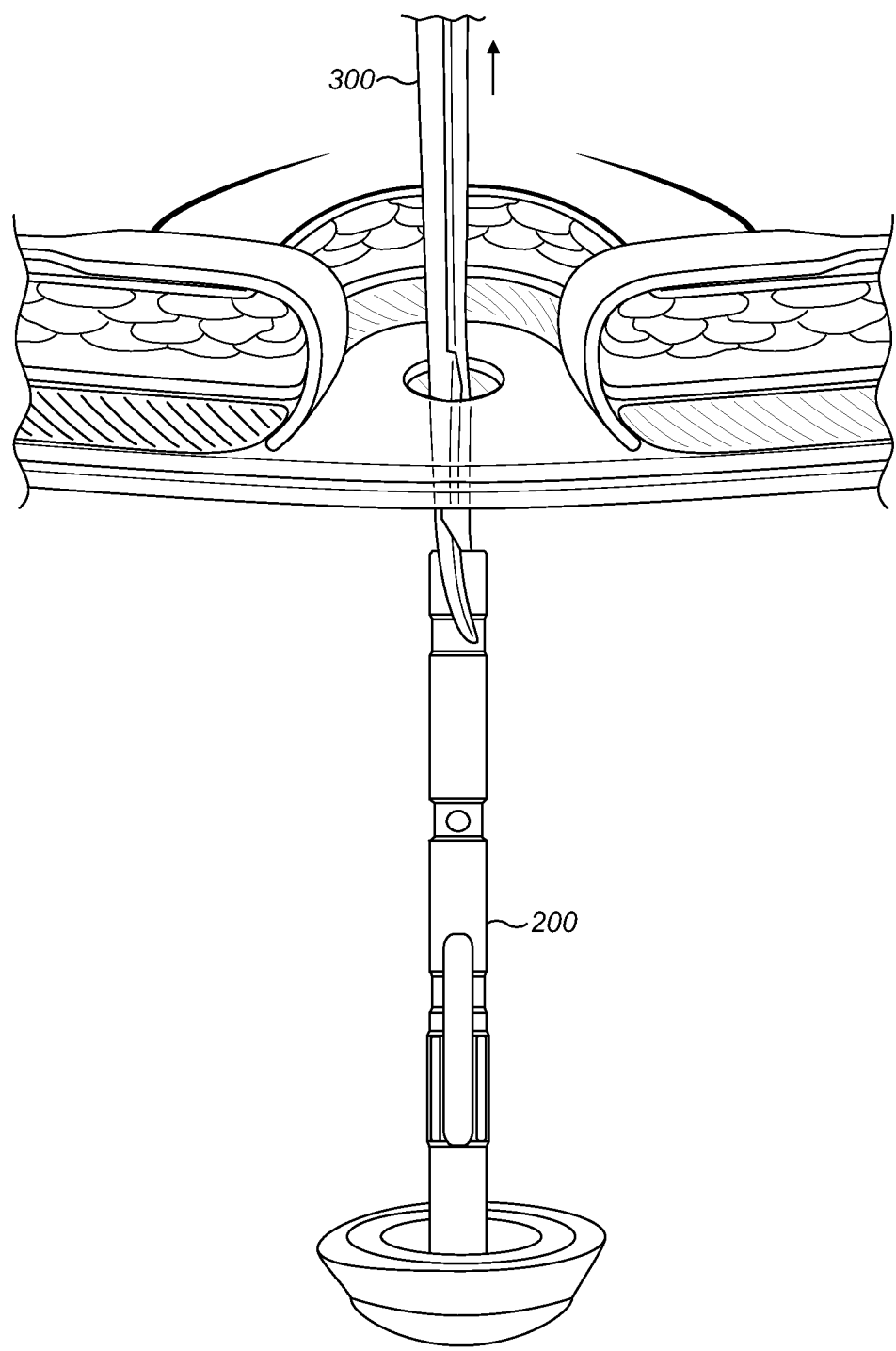
FIG. 17 shows an anvil 200 according to the invention being retrieved through the excision in the abdominal wall using forceps 300.

Forceps 300 are then inserted via the abdominal wall trephine to penetrate the posterior rectus sheath and peritoneum (FIG. 17). The forceps is used to grasp the anvil shaft and is preferably is designed not to damage it. In some embodiments, the forceps is blunted but sufficiently sharp to penetrate the layers it needs to transgress. Consequently visualisation of its tip when penetrating the abdominal wall is most preferred.

Once the anvil shaft has been grasped the anvil is then exteriorised through the trephine to emerge on the abdominal wall.

Figure 18:
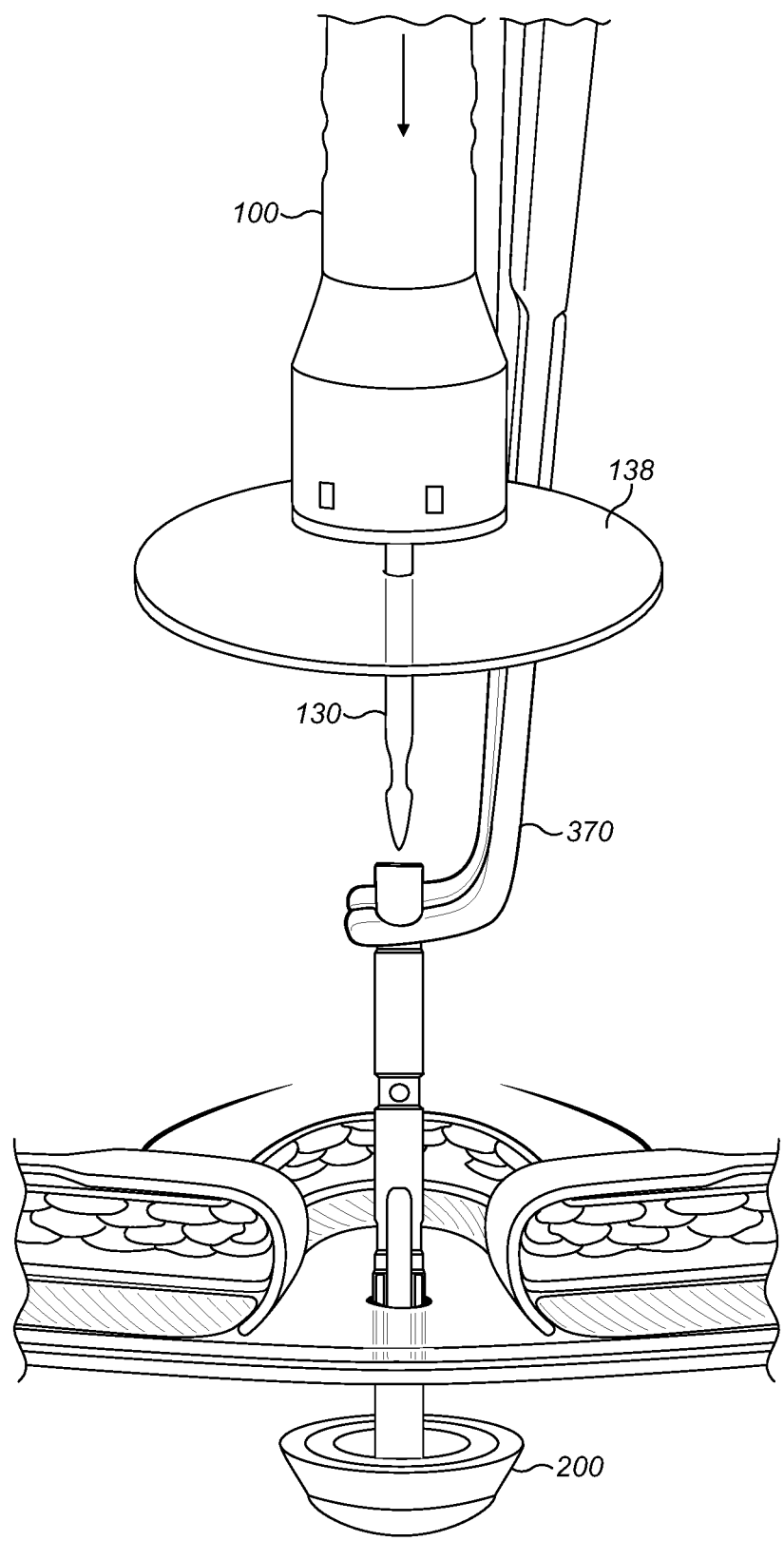
FIG. 18 shows a stapler of the invention 100 with mesh reinforcement 138 applied to the anvil docking pin 130 and the anvil 200 aligned with the anvil docking pin 130 ready for engagement. The anvil is being steadied using tongs 370.

The tongs 370 are used externally to grasp the anvil shaft and steady it and facilitate eventual mating of the anvil shaft with the anvil docking pin emanating from the stapling means (FIG. 18). A mesh 138 which is optionally configured in a circular design with a diameter greater than or equal to that of the anvil can optionally be prepared by creating a small defect in its centre. The defect in the mesh can then be utilised to insert the mesh onto the anvil docking pin 130, as show in FIG. 18.

Figure 19:
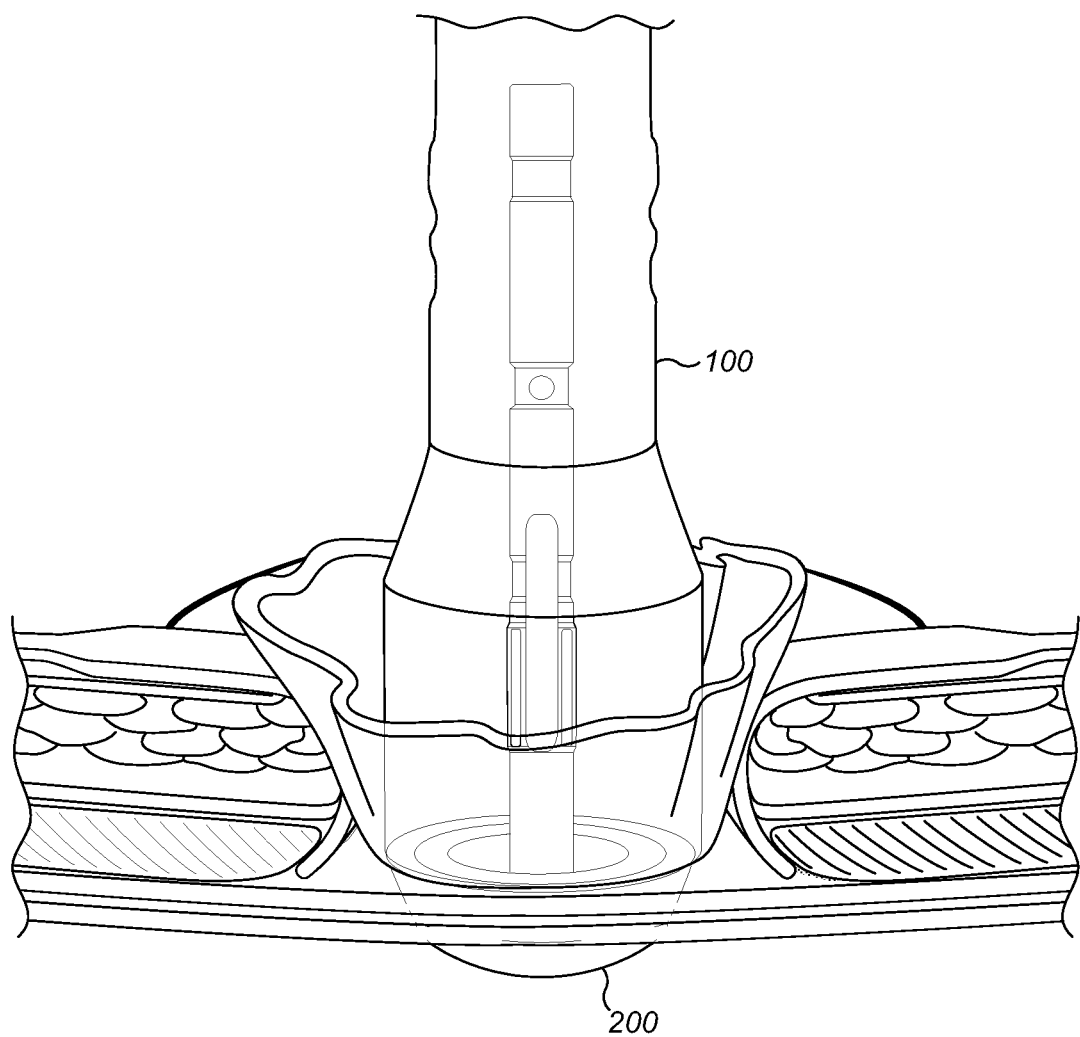
FIG. 19 shows the anvil 200 and stapler 100 fully engaged and the anvil retracted into the stapler.
Figure 20:
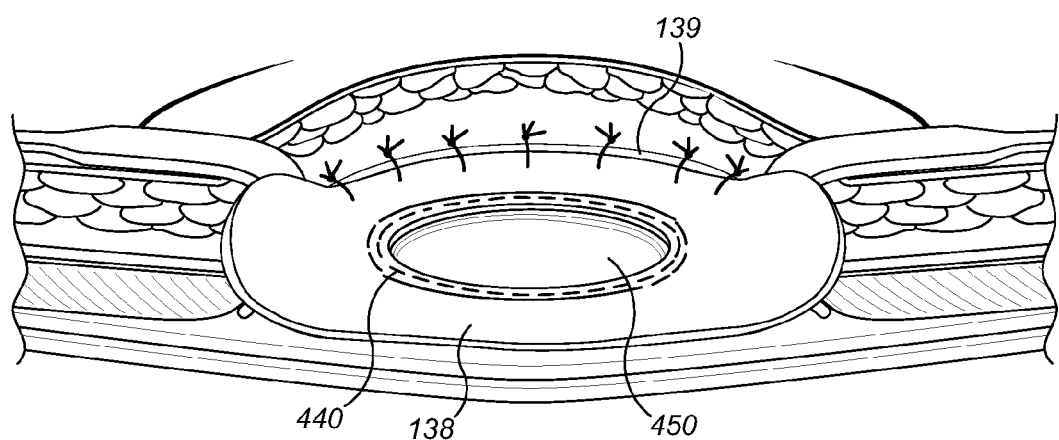
FIG. 20 shows the a row of staples 440 defining a stoma trephine 450 after actuation of the stapler and subsequent suturing of the loose rim 139 of the mesh 138.

The anvil shaft is grasped by the tongs 370 and mated with the anvil docking pin 130 of the stapler. Once successful locking has been achieved the retracting means is operated to enclose the mesh, the posterior rectus sheath and the peritoneum at the interface between the anvil head and the stapling means (FIG. 19). The trigger is then activated to actuate the stapling means before removing the stapler 100, taking with it a disc of mesh, posterior rectus sheath and peritoneum and leaving a precise reinforced stapled trephine 450 defined by a staple line 440. The rim 139 of the mesh 138 is next optionally sutured to the anterior rectus sheath with interrupted 0 PDS (polydioxanone) sutures or stapled so it lies flat against the anterior sheath and totally lines the trephine 450 through the split muscle fibres (FIG. 20).

Figure 21:
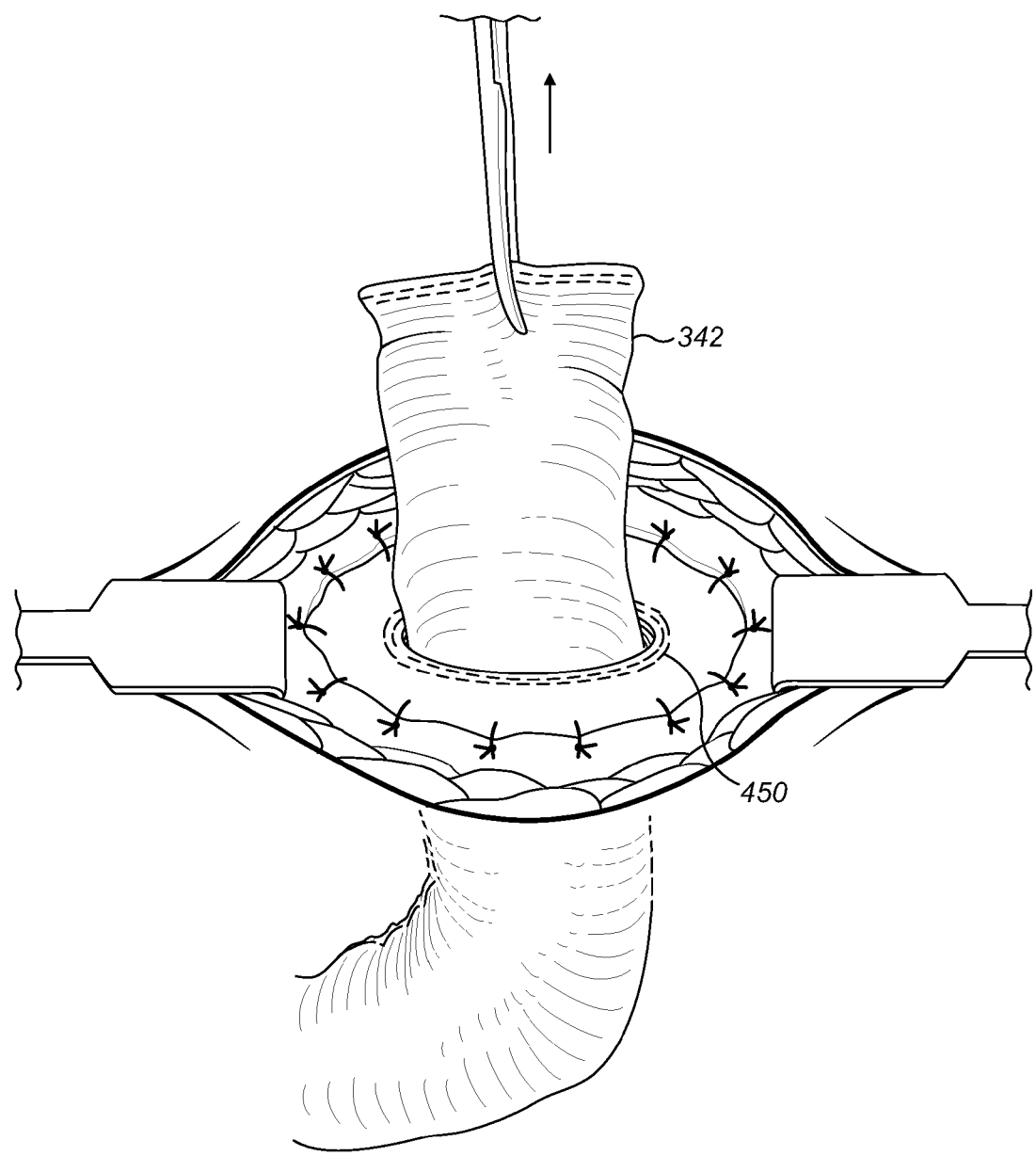
FIG. 21 shows a section of bowel 342 being retrieved through the newly created stoma trephine 450.

The colon or ileum is then drawn through the trephine and the stoma is fashioned in the usual way (FIG. 21; a description of the formation of stomas is provided in, for example, Keighley, M. R. B. & Williams, N. S., "Surgery of the Anus Rectum and Colon", 3rd Ed., Saunders Ltd., 2008: Chapter 5, pp. 175-278).

Figure 16:
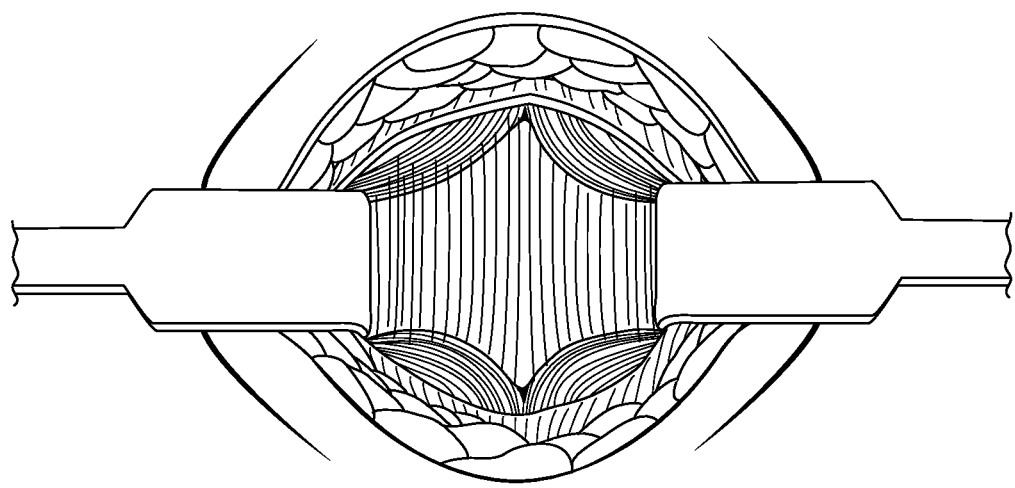
FIG. 16 shows the incision being held open using retractors (Langenbeck retractors).

In laparoscopic surgery, a stoma trephine is formed down to the posterior rectus sheath as described above for the open technique but with the pneumoperitoneum still maintained. If a separate abdominal wall incision is created for specimen retrieval the anvil shaft can be inserted into the abdominal cavity and exteriorised in the same way as for the open technique. If this is not the case the rectus muscle fibres can be retracted (as shown in FIG. 16) and a small incision made via the abdominal wall trephine in the posterior rectus sheath and peritoneum. This naturally results in deflation of the abdominal cavity as the pneumoperitoneum is lost.

Figure 22:
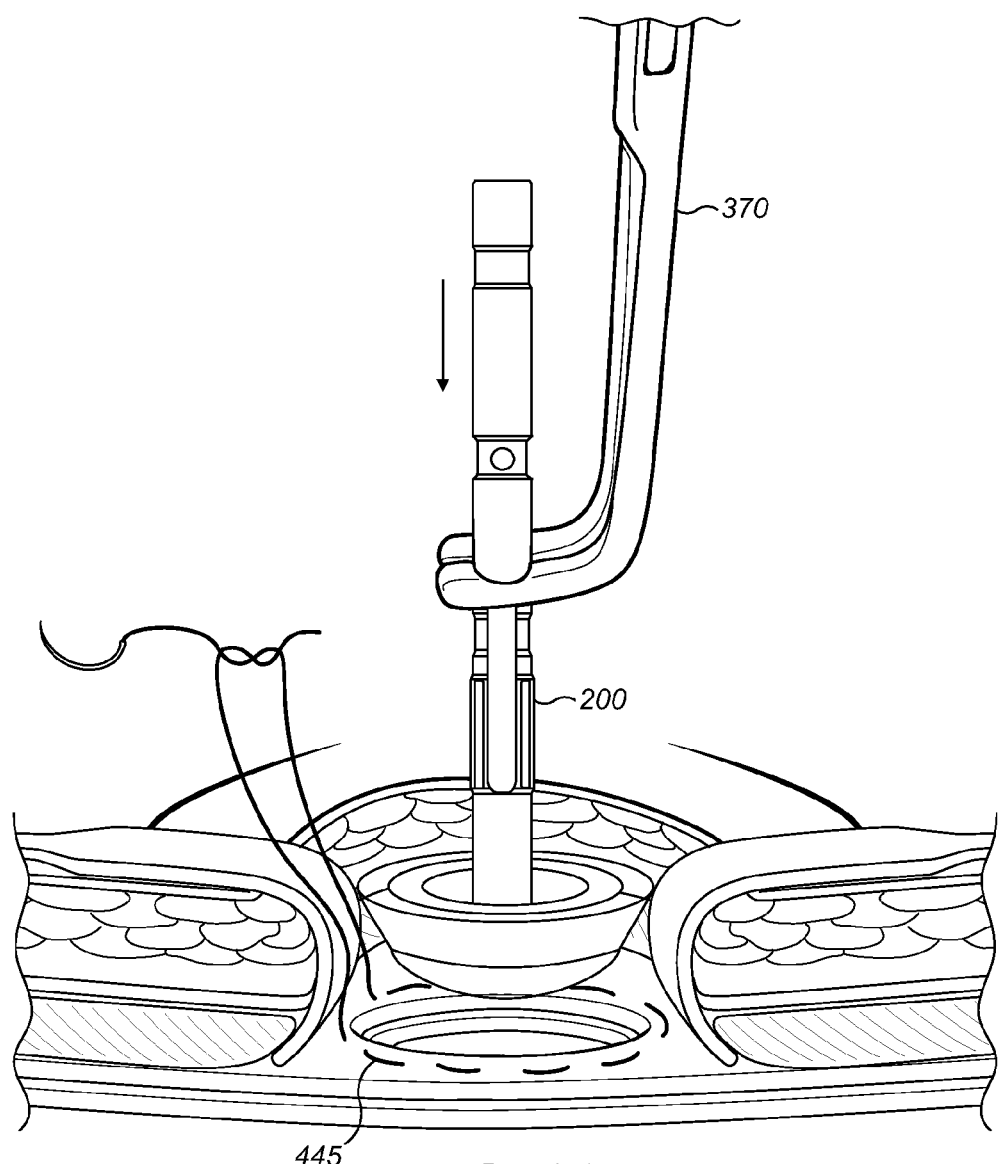
FIG. 22 shows the introduction of an anvil 200 according to the invention into the abdominal wall during a laparoscopic procedure using tongs 370. A purse string suture 445 has been formed at the rim of the incision.
Figure 23:
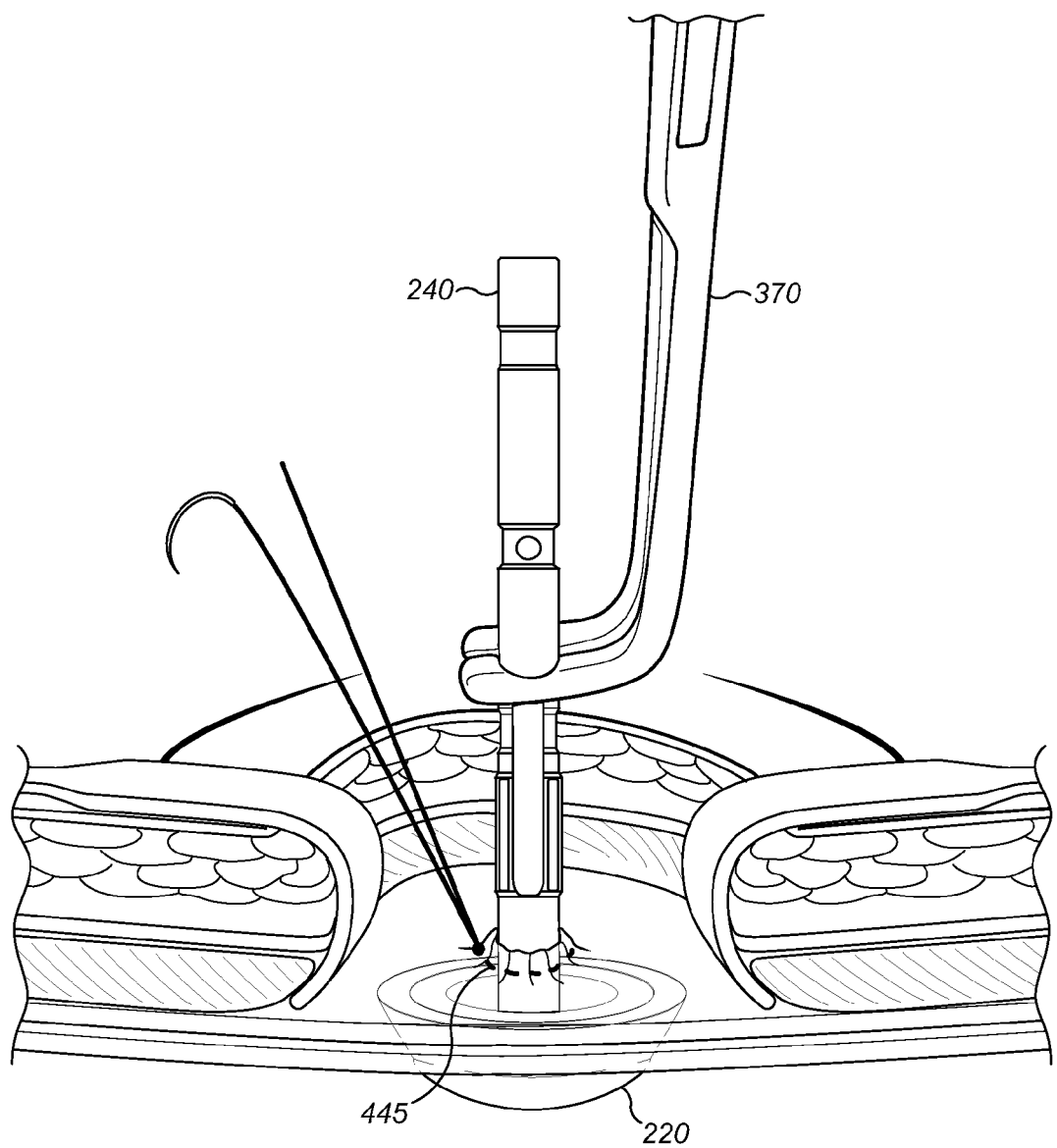
FIG. 23 shows the anvil head 220 inside the abdomen and the purse string suture 445 closed around the anvil shaft 240 prior to engagement with a stapler.

A prolene or PDS purse-string suture 445 is next inserted into the rim of the incision in the peritoneum and posterior rectus sheath (FIG. 22). The anvil head of the anvil 200 is passed through this incision using the tongs 370 with the shaft exteriorised and the purse-sting 445 is tied firmly around its base on the shaft 240 (FIG. 23).

Optionally, a circular or otherwise configured mesh is then inserted over the anvil shaft as described above. Mating between the anvil shaft and the anvil docking pin is then completed as described and the anvil docking pin is retracted (where required) by operating the retracting means.

Before activating the stapling means, the pneumoperitoneum is usually recreated and the trephine site and position of the closed gun checked to ensure no extraneous segment of bowel has been trapped between the anvil and the stapling housing of the instrument. Once the trigger is activated to actuate the stapling means, the stapler is withdrawn and the stoma constructed in the usual way (Keighley & Williams).

This technique incorporating a reinforcing mesh has been developed by the inventors and is referred to as SMART (Stapled Mesh stomA Reinforcement Technique). Previous studies that have incorporated a mesh were conducted at open surgery and the mesh is placed sub-peritoneally via an abdominal approach. Although such a technique is relatively simple it markedly increase operating time and is difficult to perform laparoscopically, and requires stretching of the tissue. The SMART technique using a stapler apparatus of the invention is simple and quick to perform, and it places the mesh in the correct layer of the abdominal wall so as to prevent adhesions. This technique is reproducible and can be performed both at open and laparoscopic surgery with ease. The stapler allows the creation of a stoma trephine and simultaneously reinforces it with a mesh. It can be used for the formation of virtually any kind of stoma, including in ileostomy and colostomy construction. The SMART technique also avoids unnecessary stretching of the tissue and so the incidence of herniation is much lower.

Use of an anvil 245 with one or a plurality of hollow channels and the suction modification described above and as shown in FIGS. 24 and 25 helps to ensure the bowel that will constitute the stoma can be withdrawn easily through the trephine and be correctly orientated. This manoeuvre is especially difficult in laparoscopic stoma formation due to restricted access to the abdominal cavity in such procedures.

The methods can be carried out in vivo in patients (either human or non-human patients). The methods can also be ex vivo methods carried out on tissue samples.

The methods of the invention can employ any stapler apparatus of the invention. For example, the methods may employ the anvil 245 comprising one or more hollow channels that extend from the anvil shaft through the entire thickness of the anvil head. Consequently, the methods may additionally comprise a step of applying suction through the anvil to manipulate the surface or tissue to be stapled. The manipulation of the tissue or surface to be stapled allows it to be positioned appropriately to facilitate formation of the anastomosis or stoma.

In a sixth aspect of the invention, there is provided a kit of parts comprising a stapler apparatus of the invention and a safety guard. The safety guard is made of plastic or metal or other suitable material and is intended to be positioned between the stapling means and the anvil docking pin with an engaged anvil during transportation. This protects the stapler apparatus from damage by preventing the stapling means from pressing against the anvil head. The safety guard can also prevent the stapler means from firing accidently, for example in those embodiments where the stapling means can only be actuated when the anvil docking pin is retracted far enough into the stapler.

The safety guard may be cylindrical and, preferably, the safety guard comprises a central hole and is attachable onto the anvil docking pin such that the anvil docking pin passes through the central hole of the safety guard. The safety guard may also include a passage from the outer edge of the safety guard to the central hole of the safety guard that allows the safety guard to be place on or removed from the anvil docking pin even when the anvil is engaged.

In a seventh aspect of the invention, there is provided a kit of parts comprising a stapler apparatus of the invention and mesh reinforcement 138. This mesh or other reinforcing material serves to reinforce the anastomosis or stoma trephine being formed since the applied staples pass through both layers of tissue and the mesh. The mesh may also improve the seal between the two layers of tissue to prevent leakage of any material from the lumen of the organ into the body cavity. The mesh can be made of any suitable material, such as a synthetic or a biological material.

Synthetic materials suitable for the mesh include polypropylene, polyester and polytetrafluoroethylene (PTFE, for examples compressed, expanded or electro spun). Polypropylene is stable, strong, inert and has good handling qualities. The polypropylene meshes are made up of polypropylene fibres arranged in a network with pores of different sizes. PTFE meshes are smooth, soft and strong and allow good tissue ingrowths.

Biological meshes include those harvested from cows, pigs and horses such as pericardium, but also other organs including dermis tissue.

Alternatively, a kit according to the invention may include a stapler apparatus of the invention, a mesh and a safety guard.

The kits according to the invention can optionally further comprise instructions for use. The kits may also further comprise forceps which can be used to manipulate the anvil shaft. For example, the forceps may be used to retrieve the anvil shaft through an incision in the abdominal wall when creating a stoma trephine. Alternatively or additionally, the forceps may aid in the docking of the anvil shaft with the anvil docking pin. The kits of the invention may comprise the tongs 370, or any combination of features, for example a stapler apparatus, a safety guard, a mesh 138 and tongs 370.

In some embodiments, the kits are sterile. The kits can also be disposable.

Features for the second and subsequent aspects of the invention are as for the first aspect, mutatis mutandis.

EXAMPLES

The invention will now be further described with reference to the following examples which are presented merely for illustrative purposes and are not intended to be limiting on the scope of the invention.

Example 1

Anterior Perineal PlanE for Ultra-Low Anterior Resection of the Rectum (the APPEAR Technique)

Fourteen patients were enrolled, 7 with neoplasia, 5 with ulcerative colitis, and 2 with traumatic rectal damage. Patients were evaluated preoperatively, and at a median of 2 years after surgery.

Nine of 14 patients underwent ileostomy reversal and were followed up for a minimum of 1 year, with 1 patient awaiting closure. Four patients had not yet been considered for ileostomy reversal due to anastomotic perineal fistulae. Transient sexual dysfunction was noted in 3 of 14 patients, but no urological problems occurred.

When the APPEAR procedure was performed for neoplasia or trauma, postoperative median Wexner continence score was 5 (range 0-8, n=6), with a median defecation frequency of 3 (range 1-8/day). All cancers were completely excised with no local recurrence. Following APPEAR with restorative proctocolectomy for ulcerative colitis, median Wexner continence score was 2 (range 0-6, n=3), with a median daily defecatory frequency of 3 (range 1-5). Preoperative SF-36 scores (36-part short form questionnaire that measures quality of life) did not change significantly following ileostomy closure, and anorectal physiological testing was unaltered following perineal dissection.

The APPEAR procedure therefore provides an alternative technique to effect an ultra-low sphincter-saving anastomosis, when this is not possible by conventional surgery. This is a promising new procedure with the potential to reduce the need for a permanent stoma even further than is currently the case. The use of a stapler apparatus of the invention in procedures such as the APPEAR technique allows endo-anal or extracorporeal docking of the anvil and stapler, allowing the surgeon to see more clearly where the anvil is to aid docking onto the anvil docking pin. The elongated shaft also allows the surgeon to see extracorporeally that the anvil has fully engaged with the stapler.

Example 2

Stapled Mesh stomA Reinforcement Technique (SMART)

Parastomal hernias (PH) are frequent with a high morbidity. Three randomised controlled trials showed that mesh reinforcement significantly reduced their incidence. The techniques however were time consuming, difficult to perform laparoscopically and relied on manual stretching of the trephine. SMART obviates these problems.

SMART uses the stapler apparatus of the invention to create a precise trephine in the posterior rectus sheath and peritoneum and simultaneously fixes mesh subperitoneally and circumferentially to the trephine. Stretching is minimised. 9 patients (M:F 2:7, median age 55 yrs range 24-77) at high risk of PH and in whom randomisation in a controlled trial was contraindicated underwent SMART (7 open: 2 laparoscopic).

There was no post-operative (30 days) morbidity related to stoma formation. All stomas functioned satisfactorily within 48 hours. One patient developed intestinal obstruction after hospital discharge unrelated to stoma formation and another developed temporary peristomal pain and swelling following successful cardiorespiratory resuscitation. During follow-up of 13 weeks (2-14), no parastomal hernia was found.

SMART is a new and simple means of precisely creating a reinforced stoma trephine at both open and laparoscopic surgery and it reduces the parastomal herniation rate.

The invention claimed is:

1. A stapler apparatus, comprising:
   (a) a stapler having a proximal end, a distal end and a longitudinal axis, the stapler further comprising:
      (i) a trigger;
      (ii) an anvil docking pin aligned parallel with the longitudinal axis of the stapler; and
      (iii) a stapling means;
   wherein the anvil docking pin and stapling means are at the distal end of the stapler; and
   (b) a detachable anvil, comprising an anvil head and an anvil shaft, wherein the anvil shaft receives the anvil docking pin and operation of the trigger causes the stapling means to be actuated, characterized in that:
   the length of the anvil shaft is at least 4 cm;
   the anvil shaft comprises an internal chamber and the anvil docking pin is inserted into the internal chamber of the anvil shaft;
   the anvil shaft comprises a viewing window and the anvil docking pin comprises a docking indicator such than when the anvil is fully docked over the anvil docking pin, the docking indicator is visible through the viewing window; and
   the anvil shaft and the anvil docking pin further comprise a retaining means that secures the anvil in position when the anvil is docked on the anvil docking pin.

2. The stapler apparatus of claim 1 wherein the anvil shaft comprises one or more indentations.

3. The stapler apparatus of claim 1, wherein the anvil shaft is between 6 and 20 cm in length.

4. The stapler apparatus of claim 1, wherein the stapling means comprises a stapler housing, a circular blade, a driving blade and one or more rows of staple slots around the outside of the circular blade in a substantially circular arrangement.

5. The stapler apparatus of claim 1, wherein the anvil head is curved, conical or frustoconical in shape.

6. The stapler apparatus of claim 1, wherein the anvil further comprises one or more hollow channels that extend from the internal chamber of the anvil shaft through the entire thickness of the anvil head and terminate in apertures in the surface of the anvil head.

7. An anvil for a stapler apparatus comprising an anvil head and an anvil shaft, characterized in that:
   the length of the anvil shaft is at least 4 cm; and
   the anvil shaft comprises an internal chamber and an anvil docking pin inserted into the internal chamber of the anvil shaft; the anvil shaft comprises a viewing window and the anvil docking pin comprises a docking indicator such that when the anvil is fully docked over the anvil docking pin, the docking indicator is visible through the viewing window; and the anvil shaft and the anvil docking pin further comprises a retaining means that secures the anvil in position when the anvil is docked on the anvil docking pin.

8. A method of forming an anastomosis between two surfaces using the stapler apparatus of claim 1, comprising:
   attaching a first surface to be stapled to the anvil of the stapler apparatus;
   engaging the anvil docking pin with the anvil shaft;
   positioning the stapler to engage the stapling means with a second surface to be stapled; and
   activating the trigger to connect together the first and second surfaces with staples.

9. The method of claim 8, further comprising the step of operating a retracting means to retract the anvil docking pin and engaged anvil into the stapler.

10. The method of claim 8, wherein the first surface to be stapled is attached to the anvil by means of a purse string suture.

11. The method of claim 8, further comprising applying a mesh to the anvil docking pin or anvil shaft.

12. A method of forming a stoma trephine in a subject using the stapler apparatus of claim 1, comprising:
   forming an incision in a tissue where a stoma is to be formed;
   positioning the anvil of the stapler apparatus such that the anvil head is inside the subject and the anvil shaft is projecting through the incision;
   docking the anvil shaft onto the anvil docking pin of the stapler; and
   activating the trigger to dispense a series of staples in the tissue being stapled.

13. The method of claim 12, further comprising the step of retrieving the anvil shaft through the incision.

14. The method of claim 12, further comprising applying a mesh to the anvil docking pin or anvil shaft.

15. The method of claim 12 further comprising the step of operating a retracting means to retract the anvil docking pin and engaged anvil into the stapler.

16. The method of claim 8, wherein the anvil comprises one or more hollow channels further that extend from the anvil shaft through the entire thickness of the anvil head and wherein the method further comprises the step of applying suction through the anvil.

17. A kit of parts comprising the stapler apparatus of claim 1, and a safety guard.

18. A kit of parts comprising the stapler apparatus of claim 1, and a mesh.

19. The kit of parts of claim 17, further comprising tongs.

20. The kit of parts of claim 19, wherein the tongs comprise a pair of symmetrical elongate members attached to each other at one end by a hinge or flexible join, the elongate members being curved at the other end and comprising one or more recesses in opposing elongate members.

21. The stapler apparatus of claim 1 wherein the anvil head, anvil shaft, anvil docking pin, and stapling means are all substantially circular in cross section.

* * * * *